United States Patent
Teff et al.

(10) Patent No.: US 8,252,704 B2
(45) Date of Patent: *Aug. 28, 2012

(54) ADDITIVES TO PREVENT DEGRADATION OF CYCLIC ALKENE DERIVATIVES

(75) Inventors: Daniel J. Teff, Chandler, AZ (US); John L. Chagolla, Mesa, AZ (US)

(73) Assignee: Fujifilm Electronic Materials U.S.A., Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,977

(22) Filed: Jul. 11, 2011

(65) Prior Publication Data

US 2011/0259242 A1 Oct. 27, 2011

Related U.S. Application Data

(60) Division of application No. 12/974,090, filed on Dec. 21, 2010, now Pat. No. 7,985,350, which is a continuation of application No. 12/498,726, filed on Jul. 7, 2009, now Pat. No. 7,871,536, which is a continuation-in-part of application No. 11/519,579, filed on Sep. 12, 2006, now Pat. No. 7,931,823, said application No. 12/498,726 is a continuation-in-part of application No. 11/519,524, filed on Sep. 12, 2006, now Pat. No. 7,883,639.

(60) Provisional application No. 60/716,102, filed on Sep. 12, 2005, provisional application No. 60/716,283, filed on Sep. 12, 2005, provisional application No. 61/078,984, filed on Jul. 8, 2008.

(51) Int. Cl.
  *H01L 21/316* (2006.01)
  *H01L 21/473* (2006.01)
  *C23C 16/44* (2006.01)
  *C23C 16/40* (2006.01)
  *C09K 15/08* (2006.01)
  *C10L 1/183* (2006.01)

(52) U.S. Cl. .................. 438/787; 252/404; 252/182.29; 44/312; 44/442; 44/443; 44/445; 427/255.6; 427/248.1; 427/255.29; 438/758; 438/778; 438/790

(58) Field of Classification Search .................. 438/778, 438/758, 787, 790; 427/248.1, 255.29; 106/287.26
See application file for complete search history.

(56) References Cited

U.S. PATENT DOCUMENTS

2,964,575 A  12/1960  Schul et al.
(Continued)

FOREIGN PATENT DOCUMENTS

JP          63174939 A      7/1988

OTHER PUBLICATIONS

Matheson Tri-Gas, Inc., "Material Safety Data Sheet", Jun. 14, 2007, Basking Ridge, NJ.

(Continued)

*Primary Examiner* — Joseph D Anthony
(74) *Attorney, Agent, or Firm* — Fish & Richardson P.C.

(57) ABSTRACT

This disclosure relates to compositions that include (a) at least one substituted or unsubstituted cyclic alkene, and (b) an antioxidant composition including at least one compound of Formula (I):

$$R^1 \text{ through } R^4 \text{ in Formula (I) are described in the specification.}$$

20 Claims, 3 Drawing Sheets

U.S. PATENT DOCUMENTS

| | | | |
|---|---|---|---|
| 2,969,399 | A | 1/1961 | Schmerling |
| 4,066,562 | A | 1/1978 | Wollensak et al. |
| 4,222,884 | A | 9/1980 | Malec |
| 4,246,367 | A | 1/1981 | Curtis, Jr. |
| 4,278,554 | A | 7/1981 | Malec |
| 4,362,848 | A | 12/1982 | Friedli et al. |
| 4,503,267 | A | 3/1985 | Pavin |
| 4,551,489 | A | 11/1985 | Bayha |
| 4,744,881 | A | 5/1988 | Reid |
| 4,745,141 | A | 5/1988 | Akiyama et al. |
| 4,979,545 | A | 12/1990 | Fair |
| 5,091,594 | A | 2/1992 | Kupper et al. |
| 5,279,338 | A | 1/1994 | Goossens |
| 5,359,023 | A | 10/1994 | Wang et al. |
| 5,372,754 | A | 12/1994 | Ono |
| 5,451,260 | A | 9/1995 | Versteeg et al. |
| 5,536,323 | A | 7/1996 | Kirlin et al. |
| 5,551,309 | A | 9/1996 | Goossens et al. |
| 5,607,002 | A | 3/1997 | Siegele et al. |
| 5,679,631 | A | 10/1997 | Bohnert et al. |
| 5,835,678 | A | 11/1998 | Li et al. |
| 5,882,416 | A | 3/1999 | Van Buskirk et al. |
| 5,973,085 | A | 10/1999 | Muhlebach et al. |
| 5,992,830 | A | 11/1999 | Daubs et al. |
| 6,040,388 | A | 3/2000 | Nishimura et al. |
| 6,063,893 | A | 5/2000 | Karasawa et al. |
| 6,159,871 | A | 12/2000 | Loboda et al. |
| 6,217,658 | B1 | 4/2001 | Orczyk et al. |
| 6,265,490 | B1 | 7/2001 | Morel-Fourrier et al. |
| 6,312,793 | B1 | 11/2001 | Grill et al. |
| 6,383,555 | B1 | 5/2002 | Hayash et al. |
| 6,437,443 | B1 | 8/2002 | Grill et al. |
| 6,479,110 | B2 | 11/2002 | Grill et al. |
| 6,541,398 | B2 | 4/2003 | Grill et al. |
| 6,583,048 | B1 | 6/2003 | Vincent et al. |
| 6,596,627 | B2 | 7/2003 | Mandal |
| 6,604,492 | B2 | 8/2003 | Porter et al. |
| 6,633,076 | B2 | 10/2003 | Krishnaraj et al. |
| 6,756,323 | B2 | 6/2004 | Grill et al. |
| 6,815,373 | B2 | 11/2004 | Singh et al. |
| 6,846,515 | B2 | 1/2005 | Vrtis et al. |
| 6,858,697 | B2 | 2/2005 | Mayorga et al. |
| 6,914,335 | B2 | 7/2005 | Andideh et al. |
| 7,101,948 | B2 | 9/2006 | Mayorga et al. |
| 7,108,771 | B2 | 9/2006 | Xu et al. |
| 7,129,311 | B2 | 10/2006 | Teff et al. |
| 7,531,590 | B2 | 5/2009 | Teff et al. |
| 7,871,536 | B2 * | 1/2011 | Teff et al. ............ 252/182.29 |
| 7,883,639 | B2 * | 2/2011 | Teff et al. ............ 252/182.29 |
| 7,931,823 | B2 * | 4/2011 | Teff et al. ............ 252/182.29 |
| 7,985,350 | B2 * | 7/2011 | Teff et al. ............ 252/182.29 |
| 2002/0037958 | A1 | 3/2002 | Benage et al. |
| 2003/0220422 | A1 | 11/2003 | Kaprinidis |
| 2004/0023453 | A1 * | 2/2004 | Xu et al. ............ 438/202 |
| 2004/0058090 | A1 * | 3/2004 | Waldfried et al. ....... 427/558 |
| 2004/0127070 | A1 | 7/2004 | Teff et al. |
| 2004/0198922 | A1 | 10/2004 | Adegawa |
| 2005/0131182 | A1 | 6/2005 | Murakami et al. |
| 2006/0009372 | A1 | 1/2006 | Mansfield et al. |
| 2006/0270787 | A1 | 11/2006 | Teff et al. |
| 2007/0057234 | A1 | 3/2007 | Teff et al. |
| 2007/0057235 | A1 | 3/2007 | Teff et al. |
| 2009/0159843 | A1 | 6/2009 | Mayorga et al. |
| 2009/0159844 | A1 | 6/2009 | Mayorga et al. |
| 2009/0297711 | A1 * | 12/2009 | Mayorga et al. ....... 427/255.29 |
| 2011/0245416 | A1 * | 10/2011 | Wada et al. ............ 524/849 |

OTHER PUBLICATIONS

Styrene Producers Association, CEFIC Sector Group, "Styrene Monomer: Environmental, Health, Safety Transport and Storage guidelines," Mar. 3, 2008, Belgium.

L. Ross C. Barclay and Melinda R. Vinqvist, "Phenols as antioxidants," *The Chemistry of Phenols*. Edited by Z. Rappoport, 2003 John Wiley & Sons, Ltd., Hoboken, NJ.

European Search Report, Apr. 18, 2006.

Clariant LSM 171779, Norbornadiene Data Sheet, created on Dec. 12, 2003 and modified on Aug. 24, 2006.

Clariant Norbornadiene Material Specification, Sep. 5, 2006.

Aldrich B33803 Bicyclo[2.2.1]hepta-2,5-diene Specification Sheet, 2009.

Aldrich Bicyclo[2.2.1]hepta-2,5-diene Specification Sheet, 2009.

B. S. Bjola, et al., "Molar Excess Volumes and Molar Excess Enthalpies of Binary Liquid Mixtures of Norbornadiene + Benzene, + Cyclohexane, + Decane, and + Carbon Tetrachloride", J. Chem. Eng. Data 2002, 47, 250-253.

Online chemical jounal "LOOKCHEM" (www.lookchem.com/cas-128/128-37-.html), for Butylated hydroxytoluene, online chemical journal accessed on Aug. 16, 2010.

Extended Search Report issued on Dec. 1, 2009 in European Application No. 06803326.5.

Extended Search Report issued on Dec. 1, 2009 in European Application No. 06803374.5.

* cited by examiner

ADDITIVES TO PREVENT DEGRADATION OF CYCLIC ALKENE DERIVATIVES

CROSS-REFERENCE TO RELATED APPLICATIONS

This application is a divisional and claims priority to U.S. application Ser No. 12/974,090, filed Dec. 21, 2010, which is a continuation and claims priority to U.S. application Ser. No. 12/498,726, filed Jul. 7, 2009, now U.S. Pat. No. 7,871,536, which is a continuation-in-part and claims priority to U.S. application Ser. No. 11/519,579, filed Sep. 12, 2006, now U.S. Pat. No. 7,931,823, which in turn claims priority to U.S. Provisional Application No. 60/716,102, filed Sep. 12, 2005. U.S. application Ser. No. 12/498,726 is also a continuation-in-part and claims priority to U.S. application Ser. No. 11/519,524, filed Sep. 12, 2006, now U.S. Pat. No. 7,883,639, which in turn claims priority to U.S. Provisional Application No. 60/716,283, filed Sep. 12, 2005. U.S. application Ser. No. 12/498,726 also claims priority from U.S. Provisional Application No. 61/078,984 filed Jul. 8, 2008. The contents of the above-referenced applications are herein incorporated by reference.

BACKGROUND OF THE DISCLOSURE

1. Field of the Disclosure

This disclosure relates generally to cyclic alkene compositions that exhibit stability to air and/or heat. More particularly, this disclosure is directed to cyclic alkene derivatives stabilized with one or more antioxidant compounds (e.g., substituted phenols) to reduce or eliminate polymer formation upon exposure of a cyclic alkene composition to oxygen, heat or the two in combination, and methods for use of such compositions to form dielectric films.

2. Background of the Disclosure

The semiconductor industry requires numerous types of thin and thick films to prepare semiconductor devices, many of which are based on silicon. The elemental composition of these films is typically some combination of silicon and carbon with various combinations of oxygen, hydrogen, and fluorine. In U.S. Pat. No. 6,914,335, Andideh et al. teach how layers can differ and can be used for different purposes, while in U.S. Pat. No. 6,846,515, Vrtis et al. teach ranges of silicon, oxygen, carbon and hydrogen for dielectric films preferred by the semiconductor industry. A frequently used process is chemical vapor deposition, and there are numerous variations of this process.

In a typical chemical vapor deposition process, a silicon containing compound is introduced into a deposition chamber containing a substrate to be coated. The silicon containing compound is then chemically or physically altered (i.e., reacted with another component, or subjected to application of an energy source such as radiation, heat (thermal CVD), or plasma (PECVD), etc.) to deposit a film on the substrate. Deposited films containing only silicon and oxygen (i.e., silicon oxide) have a dielectric constant of approximately 4 in the absence of pores, while films that also contain carbon (i.e., carbon doped silicon oxide) and/or pores often have dielectric constants lower than 4. Films with a dielectric constant below about 2.7 are preferred for newer semiconductor devices. In U.S. Pat. No. 6,583,048, Vincent et al. provide examples of chemical vapor deposition techniques, dielectric constants, and examples of films that are desirable in the semiconductor industry.

The properties of a layer deposited on a substrate, such as dielectric constant, film hardness and refractive index, are influenced by changing the composition of the chemistry that is fed into the film deposition tool and the process employed. The film properties can be tuned by changing the identity of the silicon containing compound by using a different flow gas, by using one or more different reactive gases, or by using post-deposition anneal techniques. Another means to affect the layer properties is to use a combination of silicon containing compounds or to combine a silicon containing compound(s) with one or more additive compounds. These techniques can be employed to alter the chemical composition of the film to adjust the film to the desired properties. U.S. Pat. Nos. 6,633,076, 6,217,658, 6,159,871, 6,479,110 and 6,756,323, herein incorporated by reference, give examples of how film properties are affected by changing deposition parameters or component mixtures.

An alternative use for the additive compound is to provide compounds whose fragments or atoms are only temporarily resident in the film. The film can be post-treated to drive the fragments or atoms out of the film using heat, radiation or a combination of heat or radiation and reactive gases, such as oxygen, to create pores in the resulting film. This approach affects the properties (e.g. dielectric constant) of the deposited film. The compounds employed in this manner are described as porogens.

Typical porogens used in this type of approach are predominately composed of carbon and hydrogen. Examples of some of the classes of cyclic alkene compounds of interest as porogens are described in U.S. Pat. Nos. 6,846,515 and 6,756,323.

High volume semiconductor manufacturing places stringent demands on the equipment and on the purity and stability of the chemistries that flow through the equipment. A chemical that is sent through chemical lines and a vaporizer means is expected to transport and vaporize cleanly and leave behind little or no residue during extended use. The longer a piece of equipment can operate between scheduled or unscheduled maintenance periods (e.g., to clean out or replace chemical lines or a vaporizer means that is fouled or clogged with polymeric or other residue), the more productive the tool is, making it more cost-effective. A deposition tool that must be shut down often for cleaning and maintenance is not as appealing to semiconductor manufacturing customers. Thus, continuous, long term operation of equipment is desirable. Vaporizer means can include several types of vaporization apparatuses, including, but not limited to, heated vaporizers (see, e.g., U.S. Pat. Nos. 6,604,492, 5,882,416, 5,835,678 and references therein), bubbler ampoules (see, e.g., U.S. Pat. Nos. 4,979,545, 5,279,338, 5,551,309, 5,607,002, 5,992,830 and references therein), flash evaporators (see, e.g., U.S. Pat. No. 5,536,323 and references therein) and misting apparatuses (see, e.g., U.S. Pat. Nos. 5,451,260, 5,372,754, 6,383, 555 and references therein).

1,3,5,7-Tetramethylcyclotetrasiloxane (TMCTS) is a representative silicon containing compound which can be employed to produce low k dielectric films and is an example of the difficulty in maintaining stability. Initial work to is establish reliable manufacturing processes was hampered by the product gelling at different points in the deposition process, including the chemical lines, vapor delivery lines, and within the deposition chamber. This indicated that the stability of pure TMCTS was not sufficient, and a variety of additives were studied by Teff et al. in U.S. Pat. Nos. 7,129,311 and 7,531,590, which are incorporated herein by reference. It was found that antioxidants were highly effective to stabilize TMCTS against exposure to air, specifically oxygen, for extended periods of time at ambient or elevated temperatures. When antioxidant-stabilized TMCTS is used now in semiconductor manufacturing, processes are more stable, and gel formation in a deposition tool is reduced significantly.

Norbornadiene (NBDE) is an example of a cyclic diene of interest for use as a porogen primarily due to the bond strain in its structure and its tendency to undergo thermal reactions to form volatile materials when heated (see, e.g., U.S. Pat. Nos. 6,846,515, 6,479,110, 6,437,443, and 6,312,793). NBDE and similar cyclic alkene derivatives can react with oxygen to either polymerize or oxidize, forming higher molecular weight, lower volatility materials which may or may not be soluble in the cyclic alkene monomer. This reaction can cause significant degradation of the cyclic alkene over time, even after brief air exposure at room temperature.

NBDE forms highly soluble, low volatility solid products in the presence of adventitious air, in the presence of heat, or when the two are combined. While evidence of thermal degradation has been observed in samples heated at 120° C. for 24 hours, oxidative degradation has been observed in samples kept at room temperature or samples that were heated to 80° C. or more. These are very important factors to consider, since it only takes trace oxygen (low ppb level) to form enough residue (low ppm level) to become problematic during semiconductor processing. The combined difficulty of completely eliminating oxygen from a product with the need to use heat to evaporate the product during semiconductor processing makes it nearly impossible to avoid forming low volatility residue without an effective stabilizer. This can result in accumulation of the solid product in a vaporizer means as the volatile NBDE is evaporated away. If the surface area of the vaporizer means is small, it is possible that small amounts of residue (e.g., at a milligrams level) can hinder the evaporation of NBDE, eventually causing the vaporizer means to clog with the low volatility solids. If a bubbler ampoule is employed as the vaporizer means, oxidation products could initiate a polymerization process, causing the entire contents of the bubbler to polymerize and block the flow gas inlet line. This is especially true with bubblers that are constantly heated to assist the vaporization process. The only remedy is to disassemble and clean or replace the affected vaporizer means, which is very costly and time consuming. Safety issues are also a concern if pressurized chemical lines and valves become blocked with the low volatility solid.

While NBDE is being used in semiconductor manufacturing, equipment may go idle from time to time for various reasons (e.g., power fluctuation, holiday shutdown, etc). During this idle time, a portion of product (usually <1 mL) may be kept in a heated zone at temperatures up to 85° C. for several hours or days. During this time, the product can form soluble, nonvolatile residue that will accumulate in the vaporizer when the equipment is restarted. Therefore, an effective NBDE containing composition must be thermally stable for periods of hours or days.

The standard manufacturing process for a product such as stabilized NBDE involves a significant number of chemical handling steps. Since each handling step (and subsequent storage period) is not completely free of air, product will almost always be exposed to trace amounts of oxygen during its lifetime. As mentioned previously, it takes only a trace amount of oxygen to give an unacceptable level of residue. Therefore, an effective NBDE product must also be stabilized against oxygen-induced degradation for a period of time (potentially one or more years) in order for it to have an acceptable shelf life.

The semiconductor industry requires stable, predictable and reliable products, and even a relatively low level of this decomposition is unacceptable for high volume semiconductor manufacturing. Therefore, it is necessary to find a means to stabilize NBDE to ensure that the product does not easily decompose during transport from the chemical supplier to the end-use process, even after exposure to various conditions. However, chemistry of the cyclic alkene compounds differs considerably from the chemistry of the silicon containing compounds typically employed, so it is not obvious that the same compounds that stabilize the silicon containing compounds will stabilize the cyclic alkene compounds.

TMCTS is believed to ring open and polymerize in the presence of oxygen. Further, TMCTS has Si—H bonds that are reactive with molecular oxygen (see, e.g., US Patent Application No. 20040127070 and U.S. Pat. No. 6,858,697). By contrast, NBDE will slowly oligomerize in the presence of air, but it will not gel and the ring structure remains intact during the oligomerization process. Where TMCTS can completely polymerize as a gel inside a chemical line upon exposure to air, NBDE instead forms a highly soluble, medium to high molecular weight and low volatility oligomer that is not apparent upon visual inspection, or easily detectable by gas chromatography (GC). Instead, the resulting oligomers are detected when the volatile NBDE is evaporated away to leave behind the low volatility oligomers.

NBDE and similar materials are sometimes stabilized with antioxidants, such as 2,6-di-tert-butyl-4-methoxyphenol (BHA) or 2,6-di-tert-butyl-4-methylphenol (BHT), (see Clariant LSM 171779 Norbornadiene Specification Sheet and Aldrich Catalog Number B3, 380-3). The known antioxidants for these materials have very high boiling points, (b.p. of BHT is 265° C.), and may have atoms not desired to be in incorporated into the deposited film (e.g. sulfur, nitrogen). These antioxidants are commonly added at concentrations of 0.02 to 0.25 wt % (200 to 2,500 ppm), but additives can exceed this amount when the manufacturer wants to increase shelf life. Chemical manufacturers prefer to use BHT due to its low cost and availability. However, the concentrations of these additives are higher than desired for semiconductor purposes. In U.S. Patent Application Nos. 20070057234 and 20070057235 (both herein incorporated by reference), Teff et al. demonstrated results using the antioxidant 4-methoxyphenol at lower concentrations.

SUMMARY OF THE DISCLOSURE

In one aspect, this disclosure provides a composition including (a) one or more substituted or unsubstituted cyclic alkenes, and (b) an antioxidant composition including at least one compound of Formula (I):

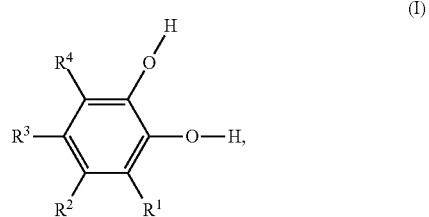

in which $R^1$ through $R^4$ can each independently be H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl.

In another aspect, this disclosure provides a composition including (a) one or more substituted or unsubstituted cyclic alkenes, and (b) an antioxidant composition including at least one compound of Formula (I), in which to $R^1$ through $R^4$ can each independently be H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl with the proviso that at least one of $R^1$ through $R^4$ is not H, and/or that, if one of $R^1$ through $R^4$ is t-butyl, at least one of the remaining $R^1$ through $R^4$ is not H. In some embodiments, the compound of Formula (I) can be 4-methyl-1,2-dihydroxybenzene or 3-methoxy-1,2-dihydroxybenzene In still another aspect, this disclosure provides a composition that includes (a) a cyclic alkene selected from the group consisting of dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene; and (b) an antioxidant composition comprising 4-methyl-1,2-dihydroxybenzene or 3-methoxy-1,2-dihydroxybenzene. The antioxidant composition is present in a concentration between about 50 ppm and about 200 ppm (e.g., 100 ppm).

In still another aspect, this disclosure provides an apparatus containing a sealed container including a cyclic alkene composition. The cyclic alkene composition contains (a) at least one substituted or unsubstituted cyclic alkene, and (b) at least one antioxidant composition, in which the cyclic alkene composition generates at most about 200 ppm (e.g., at most about 150 ppm, at most about 100 ppm, at most about 50 ppm, or at most about 10 ppm) of residue after one year of storage in the sealed container at room temperature.

In still another aspect, this disclosure provides an apparatus that includes a sealed container containing from about 0 ppm to about 150 ppm oxygen and a cyclic alkene composition. The cyclic alkene composition includes (a) at least one substituted or unsubstituted cyclic alkene, and (b) at least one antioxidant composition, in which the cyclic alkene composition generates at most about 20 ppm of residue after being heated at 80° C. for 12 hours in the sealed container. For example, when the sealed container contains about 150 ppm oxygen, the cyclic alkene composition can generate at most about 20 ppm of residue after being heated at 80° C. for 12 hours in the sealed container. As another example, when the sealed container contains about 25 ppm oxygen, the cyclic alkene composition can generate at most about 5 ppm (e.g., at most about 0.5 ppm) of residue after being heated at 80° C. for 12 hours in the sealed container. As another example, when the sealed container contains about 0 ppm oxygen, the cyclic alkene composition can generate at most about 5 ppm (e.g., at most about 0.5 ppm) of residue after being heated at 80° C. for 12 hours in the sealed container.

In still another aspect, this disclosure provides an apparatus that includes a sealed container containing from about 0 ppm to about 150 ppm oxygen and a cyclic alkene composition. The cyclic alkene composition includes (a) at least one substituted or unsubstituted cyclic alkene, and (b) at least one antioxidant composition, in which the cyclic alkene composition generates at most about 200 ppm of residue after being heated at 120° C. for 24 hours in the sealed container. For example, when the sealed container includes about 0 ppm oxygen, the cyclic alkene composition can generate at most about 200 ppm (e.g., at most about 160 ppm) of residue after being heated at 120° C. for 24 hours in the sealed container.

In still another aspect, this disclosure provides a process using a cyclic alkene composition for forming a layer of carbon-doped silicon oxide on a wafer. The process includes treating a substrate in a film deposition chamber with a composition containing at least one of the above-mentioned cyclic alkene compositions and at least one silicon containing compound to form a carbon doped silicon oxide film on the substrate. The composition can also include other additives. The process can further include, prior to the treatment step, providing the cyclic alkene composition in a first container, the silicon containing compound in a second container, a film deposition tool containing the film deposition chamber, a gas delivery line for connecting the first and second containers to the film deposition chamber within the film deposition tool, and a stream of carrier gas to sweep the cyclic alkene composition and the silicon containing compound through the gas delivery line into the film deposition chamber; introducing vapors of the cyclic alkene composition and the silicon containing compound into the carrier gas stream; and transporting the vapors of the cyclic alkene composition and silicon containing compound into the film deposition chamber via the carrier gas stream.

In still another aspect, this disclosure provides a process that includes storing at least one of the above-mentioned cyclic alkene compositions in a sealed container for at least 6 months (e.g., at least 9 months or at least one year), and after storing the cyclic alkene composition, using the cyclic alkene composition together with at least one silicon-containing compound in a chemical vapor deposition process to form a carbon doped silicon oxide film on a substrate.

In still another aspect, this disclosure provides a process for stabilizing a cyclic alkene. The process includes adding at least one compound of Formula (I) described above to the cyclic alkene. In some embodiments, adding at least one compound of Formula (I) can be carried out by, among other steps, (a) adding the at least one compound of Formula (I) in a receiving vessel in a distillation system for purifying the cyclic alkene, and (b) distilling the cyclic alkene through the distillation system into the receiving vessel. In some embodiments, adding at least one compound of Formula (I) can be carried out by, among other steps, (a) adding the at least one compound of Formula (I) at a point between a condenser and a receiving vessel in a distillation system for purifying the cyclic alkene, and (b) distilling the cyclic alkene through the distillation system so that the distilled cyclic alkene passes from the condenser into the receiving vessel, thereby solubilizing the at least one compound of Formula (I) in the distilled cyclic alkene. In some embodiments, adding at least one compound of Formula (I) can be carried out by, among other steps, (a) distilling the cyclic alkene through a distillation system into a receiving vessel, and (b) adding the at least one compound of Formula (I) into the receiving vessel.

DETAILED DESCRIPTION OF THE DISCLOSURE

Figure 1:
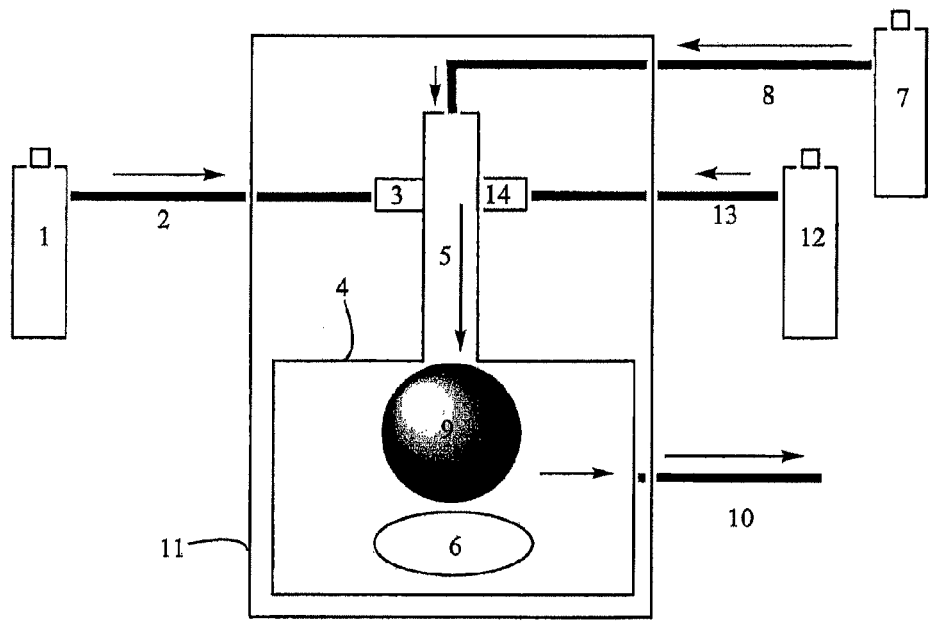
FIG. 1 is a representation of a film deposition tool used in the semiconductor industry for use with the compositions according to this disclosure, where two independent vaporizer means are used with two separate precursors.

The semiconductor industry requires numerous types of thin and thick films to prepare semiconductor devices. A frequently used process to prepare these films is chemical vapor deposition and there are numerous variations of this process. In a typical chemical vapor deposition process, a silicon containing compound is introduced into a deposition chamber containing the substrate to be coated. The silicon containing compound is then chemically or physically altered (reacted with another component, or subjected to application of an energy source such as radiation, heat (thermal CVD), or plasma (PECVD), etc.) to deposit the film on the substrate.

These purity and stability requirements are often difficult to achieve. Many materials may oxidize, polymerize or rearrange to some degree. Even small amounts (e.g., more than 200 ppm) of such byproducts may be undesirable for many semiconductor applications. Thus materials used in the semiconductor industry may require additives to prevent formation of undesired side reactions before reaching a deposition chamber.

Cyclic alkenes are materials of interest as reagents for chemical vapor deposition to form low k dielectric films in the semiconductor industry but require additives to be stabilized to maintain high purity during the shelf life of the product.

Chemicals, including additives, that are useful for the semiconductor industry are typically limited to species that have a boiling point lower than 300° C. Furthermore, the specific application in the semiconductor industry may dictate additional properties of the precursor must have. For example, formation of interlayer dielectric (ILD) films restricts precursor selection to use only silicon, oxygen, carbon and hydrogen due to compatibility issues with surrounding layers in a chip. The selection of radical inhibitors must also follow this basis, so nitrogen, sulfur and phosphorous that are found in common radical inhibitors and antioxidants such as lecithin and lipoic acid must be avoided.

In some embodiments, it is advantageous to minimize the boiling point difference between the cyclic alkenes and the stabilizer that is used. For example, NBDE boils at 89° C. while BHT boils at 265° C. This difference is enough to cause significant problems in a semiconductor deposition tool vaporizer means. Commonly, these vaporizer means are set at the lowest possible temperature to allow complete vaporization of a liquid product while avoiding thermal decomposition. It is also necessary to balance thermal loading of the vaporizer means to correctly vaporize the product without saturating a vapor stream. With these considerations, it is a fine balance to vaporize the source chemical without adding too much heat. Thus, it is most often the case that higher molecular weight components are poorly vaporized, or not vaporized at all, and these tend to accumulate in the vaporizer means to eventually clog it. For this reason, it is desirable to reduce the difference between the boiling points of cyclic alkene derivatives and their stabilizers, and to reduce the concentrations of the stabilizers to their lowest effective levels.

This disclosure relates to cyclic alkene compositions that are stabilized by the addition of specific unsubstituted or substituted dihydroxybenzene compounds surprisingly found to have higher stabilizing capability than prior art monohydroxybenzene compounds. The resulting compositions exhibit enhanced stability and significantly extend the shelf life of cyclic alkene products, allowing greater flexibility in handling these products in semiconductor manufacturing. The resulting stabilization of cyclic alkenes using more active stabilizers reduces the formation of soluble polymers in the final product. In turn, this drastically reduces the accumulation of soluble polymers in chemical delivery lines, in valves, or in vaporizer means. This reduces the need for equipment maintenance, reduces costs and reduces time the machinery is out of use for production. In addition, reducing the formation of higher molecular weight compounds allows for homogeneous vaporization of the product without concern for the gradual deposition of higher molecular weight compounds in vapor delivery lines, leading to more consistent, higher quality deposited films on the wafer. In some embodiments, the use of more volatile antioxidants (e.g., antioxidants with a relative low melting or boiling point) is also advantageous, since there is a greater likelihood that the cyclic alkene and the volatile stabilizer will be cleanly evaporated and cleanly delivered through a chemical delivery line, leading to a cleaner process. For example, when a chemical delivery line is heated so that the cyclic alkene composition can be delivered as a liquid or a vapor, the heating may not be uniform and homogeneous resulting in undesirable cold spots where the temperature is lower than in the rest of the delivery line. Even in the presence of such cold spots, an antioxidant with a lower melting or boiling point can stay liquefied or vaporized, thereby reducing contamination of the delivery line at the cold spots by the antioxidant during the delivery process.

In one embodiment of this disclosure, the cyclic alkene composition includes (a) one or more substituted or unsubstituted cyclic alkenes, and (b) an antioxidant compound shown in Formula (I),

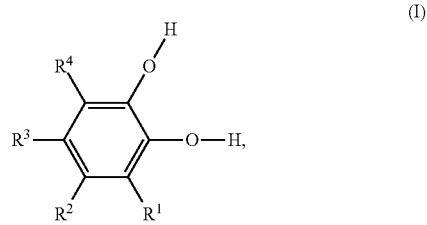

in which $R^1$ through $R^4$ can each independently be H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl with the proviso that at least one of $R^1$ through $R^4$ is not H, and that, if one of $R^1$ through $R^4$ is t-butyl, at least one of the remaining $R^1$ through $R^4$ is not H.

Cyclic alkene is hereby defined as any carbocyclic compound having a nonaromatic double bond in a nonaromatic ring. Examples of classes of cyclic alkene include, but are not limited to cycloalkenes, cycloalkadienes, cycloalkatrienes, cycloalkatetraenes, aromatic-containing cycloolefins, polycyclic alkenes, polycyclic alkadienes, polycyclic alkatrienes, polycyclic alkatetraenes, and mixtures thereof.

A preferred class of cyclic alkenes are singly or multiply unsaturated cyclic alkenes of the general formula $C_nH_{2n-2x-y}R_y$ where n is the number of carbons in the primary cyclic structure, x is the number of unsaturated sites in the primary cyclic structure, and y is the number of substituents, R, on the primary cyclic structure. In this class of cyclic alkenes, n ranged from 4 to 18, x is an integer and $1 \leq x \leq n/2$, y is an integer and $0 \leq y \leq 2n-2x$, and each R can independently be $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent. Examples of this class include, but are not limited to, t-butylcyclohexene, alpha-terpinene, limonene, gamma-terpinene, 1,5-dimethyl-1,5-cyclooctadiene, vinylcyclohexene, cyclobutene, methylcyclobutene, dimethylcyclobutene, trimethylcyclobutene, ethylcyclobutene, diethylcyclobutene, triethylcyclobutene, methoxycyclobutene, methylmethoxycyclobutene, cyclohexylcyclobutene, isopropylcyclobutene, isopropenylcyclobutene, cyclopentene, methylcyclopentene, dimethylcyclopentene, trimethylcyclopentene, methoxycyclopentene, methylmethoxycyclopentene, cyclohexylcyclopentene, isopropylcyclopentene, isopropenylcyclopentene, cyclopentadiene, methylcyclopentadiene, dimethylcyclopentadiene, trimethylcyclopentadiene, methoxycyclopentadiene, methylmethoxycyclopentadiene, cyclohexylcyclopentadiene, isopropylcyclopentadiene, isopropenylcyclopentadiene, cyclohexene, methylcyclohexene, dimethylcyclohexene, trimethylcyclohexene, methoxycyclohexene, methoxymethylcyclohexene, cyclohexylcyclohexene, isopropylcyclohexene, isopropenylcyclohexene, cyclohexadiene, methylcyclohexadiene, dimethylcyclohexadiene, trimethylcyclohexadiene, methoxycyclohexadiene, methoxymethylcyclohexadiene, cyclohexylcyclohexadiene, isopropylcyclohexadiene, isopropenylcyclohexadiene, cycloheptene, methylcycloheptene, dimethylcycloheptene, trimethylcycloheptene, methoxycycloheptene, methoxymethylcycloheptene, cyclohexylcycloheptene, isopropylcycloheptene, isopropenylcycloheptene, cycloheptadiene, methylcycloheptadiene, dimethylcycloheptadiene, trimethylcycloheptadiene, methoxycycloheptadiene, methoxymethylcycloheptadiene, cyclohexylcycloheptadiene, isopropylcycloheptadiene, isopropenylcycloheptadiene, cycloheptatriene, methylcycloheptatriene, dimethylcycloheptatriene, trimethylcycloheptatriene, methoxycycloheptatriene, methoxymethylcycloheptatriene, cyclohexylcycloheptatriene, isopropylcycloheptatriene, isopropenylcycloheptatriene, cyclooctene, methylcyclooctene, dimethylcyclooctene, trimethylcyclooctene, methoxycyclooctene, methoxymethylcyclooctene, cyclohexylcyclooctene, isopropylcyclooctene, isopropenylcyclooctene, cyclooctadiene, methylcyclooctadiene, dimethylcyclooctadiene, trimethylcyclooctadiene, methoxycyclooctadiene, methoxymethylcyclooctadiene, cyclohexylcyclooctadiene, isopropylcyclooctadiene, isopropenylcyclooctadiene, cyclooctatriene, methylcyclooctatriene, dimethylcyclooctatriene, trimethylcyclooctatriene, methoxycyclooctatriene, methoxymethylcyclooctatriene, cyclohexylcyclooctatriene, isopropylcyclooctatriene, isopropenylcyclooctatriene, cyclooctatetraene, methylcyclooctatetraene, dimethylcyclooctatetraene, trimethylcyclooctatetraene, methoxycyclooctatetraene, methoxymethylcyclooctatetraene, cyclohexylcyclooctatetraene, isopropylcyclooctatetraene, isopropenylcyclooctatetraene, 3-phenyl-1-cyclohexene, 3-(2-methoxyphenyl)-1-cyclohexene, 3-cyclohexenyltrimethylsilane, 3-cyclohexenyltrimethoxysilane, [2-(3-cyclohexenyl)ethyl]trimethoxysilane, [2-(3-cyclohexenyl)ethyl]triethoxysilane, tert-butylcyclohexene, p-menth-1-ene, phellandrene, and terpinolene.

Another preferred class of suitable cyclic alkenes is bicyclic alkenes of the general formula $C_nH_{2n-(2x+2)-y}R_y$ where n is the number of carbons in the primary bicyclic structure, x is the number of unsaturated sites in the primary bicyclic structure, and y is the number of substitutions, R, on the primary bicyclic structure. In this class of cyclic alkenes, n can range from 5 to 18, x is an integer and $x \leq n/2$, y is an integer and $0 \leq y \leq 2n-(2x+2)$, and each R can independently be $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent. Examples of this class include, but are not limited to, 3-carene, alpha-pinene, norbornene, norbornadiene, bicyclo[2.2.2]octa-2,5,7-triene, [(bicycloheptenyl)ethyl]trimethoxysilane, hexamethyldewarbenzene, bicyclo[4.3.0]nona-3,7-diene, 1,4,5,8-tetrahydronaphthalene, 2,3-dimethyl-1,4,5,8-tetrahydronaphthalene, bicyclo[4.3.0]nona-3,7-diene, bicyclo[4.1.1]oct-3-ene, bicyclo[4.2.0]oct-3-ene, bicyclo[4.2.0]octa-2,4-diene, 5-(bicyclo[2.2.1]hept-2-enyl)triethoxysilane, bicyclo[4.2.0]octa-2,7-diene, bicyclo[4.3.0]nona-3,6-diene,5-vinyl-2-norbornene and 5-ethylidene-2-norbornene.

Another preferred class of cyclic alkenes is tricyclic alkenes of the general formula $C_nH_{2n-(2x+4)-y}R_y$ where n is the number of carbons in the primary tricyclic structure, x is the number of unsaturated sites in the primary tricyclic structure, and y is the number of substitutions, R, on the primary tricyclic structure. In this class, n can range from 7 to 18, x is an integer and $x \leq n/2$, y is an integer and $0 \leq y \leq 2n-(2x+4)$, each R can independently be $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent. Examples include, but are not limited to, dicyclopentadiene, 1,2,3,4,4A,5,8,8A-octahydro-1,4-methanonaphthalene, octamethyltricyclo[4.2.0.0(2,5)]octa-3,7-diene, 1,4-dihydro-1,4-methanonaphthalene and [4.2.2]propella-2,4,7,9-tetraene.

Examples of R in each of the three classes of preferred cyclic alkenes described above include, but are not limited to, methyl, ethyl, propyl, isopropyl, isopropenyl, butyl, phenyl, methylphenyl, trimethylsilyl, cyclohexyl, methoxy, ethoxy, propoxy, isopropoxy, isopropenoxy, butoxy, phenoxy, methylphenoxy, trimethylsiloxy, or cyclohexloxy. Preferred examples of R include methyl, isopropyl, and isopropenyl. Methyl, isopropyl and isopropenyl are most preferred for R for use in semiconductor applications.

Preferred cyclic alkenes include dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene. The most preferred cyclic alkenes are dicyclopentadiene, alpha-terpinene, norbornene, norbornadiene, 5-vinyl-2-norbornene, and 5-ethylidene-2-norbornene.

Suitable antioxidants of the present disclosure are described by Formula (I), in which $R^1$ through $R^4$ can each independently be H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl with the proviso that $R^1$ through $R^4$ do not all equal H and that if one of $R^1$ through $R^4$ is t-butyl, at least one of the remaining $R^1$ through $R^4$ is not H. Preferred ranges of $R^1$ through $R^4$ in Formula (I) include H, $C_1$-$C_3$ linear alkyl, $C_3$-$C_4$ branched alkyl, and $C_1$-$C_2$ linear alkoxy considering the aforementioned proviso. More preferred ranges of $R^1$ through $R^4$ in Formula (I) include H, $C_1$-$C_2$ linear alkyl, $C_4$ branched alkyl, and $C_1$ linear alkoxy considering the aforementioned proviso. Most preferred ranges of $R^1$ through $R^4$ in Formula (I) include H, $C_1$ linear alkyl, $C_4$ branched alkyl, and $C_1$ linear alkoxy considering the aforementioned proviso. Examples of suitable $R^1$ through $R^4$ include, but are not limited to, H, methyl, ethyl, propyl, isopropyl, butyl, isobutyl, tert-butyl, cyclohexyl, methoxy, ethoxy, propoxy, isopropoxy, butoxy, isobutoxy tert-butoxy, cyclohexyloxy, phenyl or methylphenyl. Preferred examples of $R^1$ through $R^4$ in Formula (I) include H, methyl, ethyl, methoxy, ethoxy, propyl, isopropyl, isobutyl, and tert-butyl. More preferred examples of $R^1$ through $R^4$ in Formula (I) include H, methyl, ethyl, methoxy, and tert-butyl. Most preferred examples of $R^1$ through $R^4$ in Formula (I) include H, methyl, methoxy and tert-butyl.

Suitable examples of Formula (I) include, but are not limited to, 3-methyl-1,2-dihydroxybenzene, 4-methyl-1,2-dihydroxybenzene (4-MCAT, which has a boiling point of about 251° C.), 3-ethyl-1,2-dihydroxybenzene, 4-ethyl-1,2-dihydroxybenzene, 3-propyl-1,2-dihydroxybenzene, 4-propyl-1,2-dihydroxybenzene, 3-isopropyl-1,2-dihydroxybenzene, 4-isopropyl-1,2-dihydroxybenzene, 3-butyl-1,2-dihydroxybenzene, 4-butyl-1,2-dihydroxybenzene, 3-isobutyl-1,2-dihydroxybenzene, 4-isobutyl-1,2-dihydroxybenzene, 3-cyclohexyl-1,2-dihydroxybenzene, 4-cyclohexyl-1,2-dihydroxybenzene, 3-methoxy-1,2-dihydroxybenzene (3-MOCAT), 4-methoxy-1,2-dihydroxybenzene, 3-ethoxy-1,2-dihydroxybenzene, 4-ethoxy-1,2-dihydroxybenzene, 3-propoxy-1,2-dihydroxybenzene, 4-propoxy-1,2-dihydroxybenzene, 3-isopropoxy-1,2-dihydroxybenzene, 4-isopropoxy-1,2-dihydroxybenzene, 3-butoxy-1,2-dihydroxybenzene, 4-butoxy-1,2-dihydroxybenzene, 3-isobutoxy-1,2-dihydroxybenzene, 4-isobutoxy-1,2-dihydroxybenzene, 3-tert-butoxy-1,2-dihydroxybenzene, 4-tert-butoxy-1,2-dihydroxybenzene, 3-cyclohexyloxy-1,2-dihydroxybenzene, 4-cyclohexyloxy-1,2-dihydroxybenzene, 3-phenyl-1,2-dihydroxybenzene, 4-phenyl-1,2-dihydroxybenzene, 3-(4-methylphenyl)-1,2-dihydroxybenzene, 4-(4-methylphenyl)-1,2-dihydroxybenzene, 3-tert-butyl-4-methyl-1,2-dihydroxybenzene, 3-methyl-4-tert-butyl-1,2-dihydroxybenzene, 3-tert-butyl-4-methoxy-1,2-dihydroxybenzene, 3-methoxy-4-tert-butyl-1,2-dihydroxybenzene, 3-allyl-4-methoxy-1,2-dihydroxybenzene, 3-methoxy-4-allyl-1,2-dihydroxybenzene, 3-allyl-4-methyl-1,2-dihydroxybenzene, 3-methyl-4-allyl-1,2-dihydroxybenzene, 3,4-dimethyl-1,2-dihydroxybenzene, 3,6-dimethyl-1,2-dihydroxybenzene, 3,5-dimethyl-1,2-dihydroxybenzene, 3,6-dimethyl-4,5-dimethoxy-1,2-dihydroxybenzene and 4-methyl-3-methoxy-dihydroxybenzene. Preferred antioxidants of Formula (I) include 3-methyl-1,2-dihydroxybenzene, 4-methyl-1,2-dihydroxybenzene, 3-methoxy-1,2-dihydroxybenzene, 4-methoxy-1,2-dihydroxybenzene, 3-propyl-1,2-dihydroxybenzene, 4-propyl-1,2-dihydroxybenzene, 3-isopropyl-1,2-dihydroxybenzene, 4-isopropyl-1,2-dihydroxybenzene, 3-isobutyl-1,2-dihydroxybenzene, 4-isobutyl-1,2-dihydroxybenzene, 3-tert-butyl-4-methyl-1,2-dihydroxybenzene, 4-tert-butyl-3-methyl-1,2-dihydroxybenzene, 3,4-dimethyl-1,2-dihydroxybenzene, 3,6-dimethyl-1,2-dihydroxybenzene, 3,5-dimethyl-1,2-dihydroxybenzene, 3-ethyl-1,2-dihydroxybenzene, 4-ethyl-1,2-dihydroxybenzene, 3-ethoxy-1,2-dihydroxybenzene, and 4-ethoxy-1,2-dihydroxybenzene. More preferred antioxidants of Formula (I) are 3-methyl-1,2-dihydroxybenzene, 4-methyl-1,2-dihydroxybenzene, 3-ethyl-1,2-dihydroxybenzene, 4-ethyl-1,2-dihydroxybenzene, 3-methoxy-1,2-dihydroxybenzene, 4-methoxy-1,2-dihydroxybenzene, 3-tert-butyl-4-methyl-1,2-dihydroxybenzene, 4-tert-butyl-3-methyl-1,2-dihydroxybenzene, 3,4-dimethyl-1,2-dihydroxybenzene, 3,6-dimethyl-1,2-dihydroxybenzene, and 3,5-dimethyl-1,2-dihydroxybenzene. Most preferred antioxidants of Formula (I) are 3-methyl-1,2-dihydroxybenzene, 4-methyl-1,2-dihydroxybenzene, 3-methoxy-1,2-dihydroxybenzene, 4-methoxy-1,2-dihydroxybenzene, 3-tert-butyl-4-methyl-1,2-dihydroxybenzene, 4-tert-butyl-3-methyl-1,2-dihydroxybenzene, 3,4-dimethyl-1,2-dihydroxybenzene, 3,6-dimethyl-1,2-dihydroxybenzene, and 3,5-dimethyl-1,2-dihydroxybenzene.

A suitable concentration of an antioxidant of Formula (I) can range from about 1 ppm to about 200 ppm. Suitable concentration ranges can be defined by defining a low end of suitable concentrations and a high end of suitable concentrations.

The low end of the suitable concentration range for an antioxidant of Formula (I) can be any value from about 1 ppm to about 50 ppm. For example, suitable concentrations for the low end concentration range include, but are not limited to, 1 ppm, 5 ppm, 10 ppm, 25 ppm and 50 ppm. If the amount of the antioxidant is too small, the antioxidant may not provide enough stabilization effect to the composition to be stabilized.

The high end of the suitable concentration range can be limited by some considerations, such as the deposited film purity, the amount of impurity in an antioxidant of Formula (I), and solubility of an antioxidant of Formula (I) in the cyclic alkene composition. For example, because an antioxidant could itself contain impurity, including a large amount of the antioxidant into a composition could introduce a large amount of impurity, thereby resulting in a decrease in the stability of the composition. A high end of the concentration of an antioxidant of Formula (I) can be any value from about 100 ppm to about 200 ppm. Examples of suitable high end concentrations include, but are not limited to, 100 ppm, 125 ppm, 150 ppm, 175 ppm and 200 ppm.

Suitable concentration ranges may vary depending on the specific antioxidant employed and the specific process used. Examples of suitable concentration ranges include from about 1 ppm to about 200 ppm, from about 1 ppm to about 150 ppm, from about 1 ppm to about 100 ppm. Other suitable concentration ranges would include from about 10 ppm to about 200 ppm, from about 10 ppm to about 175 ppm, from about 10 ppm to about 125 ppm, and from about 10 ppm to about 100 ppm. Other suitable concentration ranges would include from about 25 ppm to about 200 ppm, from about 25 ppm to about 175 ppm, from about 25 ppm to about 125 ppm, and from about 25 ppm to about 100 ppm. Other suitable concentration ranges would include from about 50 ppm to about 200 ppm, from about 50 ppm to about 175 ppm, from about 50 ppm to about 150 ppm, from about 50 ppm to about 125 ppm, and from about 50 ppm to about 100 ppm.

The stabilized cyclic alkene composition can include a single antioxidant of Formula (I) or a mixture of such antioxidants. The mixture of antioxidants may be in any relative proportion, and may further include phenolic additives (e.g., a monohydroxybenzene) represented by Formula (II):

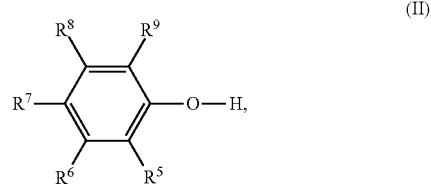

in which $R^5$ through $R^9$ can each independently be H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl. Examples of suitable substituents and preferred substituents are the same as previously described for Formula (I).

The cyclic alkenes can be obtained commercially or by synthetic techniques known to those in the art. In commercial materials, chemical manufacturers who make cyclic alkenes will often stabilize their products with relatively high concentrations of BHT. Since most manufacturers are not accustomed to making high purity products, their product handling techniques can be relatively poor, and air, moisture and other contaminants can possibly enter the container before, during or after filling. These contaminants, once closed off into the container, can cause considerable degradation to the product if it is stored for any length of time. For semiconductor purposes, the commercial materials must be purified to remove all byproducts, and additives, usually by distillation or sublimation.

However, to maintain purity and stabilization during purification, storage and shipping, the cyclic alkene and compositions of the present disclosure must be handled under strictly controlled conditions. These may include: addition of a stabilizer to a product receiver prior to distillation so that a product is immediately stabilized once it enters the product receiver, performing distillations under dry, inert atmospheres, rigorously cleaning and drying containers before use, using closed-filling techniques that prevent the product from being exposed to air, filling in a cleanroom to avoid dust and trace metal contamination that could act as polymerization catalysts, and carefully choosing containers to prevent exposure to air or other incompatible materials.

Stabilization of the cyclic alkene prior to purification is as important as stabilization of the product during and after purification. While a raw material selected for purification may already contain a stabilizer such as BHT that was added by the manufacturer, it is common for stabilizer quality and concentration to degrade during storage. In this instance, it can be helpful to add an additional stabilizer or a mixture of stabilizers to the raw material to consume impurities prior to and during the purification process.

Since oxygen may be present in the raw material and in distillation equipment in some quantity, it may have the propensity to react with unstabilized cyclic alkene in the vapor phase during a distillation. If this reaction were to occur and if the resulting impurity condensed in a refluxing process, the condensate may return to the distillation flask. There, it may combine with stabilizer and become deactivated before it has the opportunity to cause residue formation. Following this same logic, it is also important to immediately stabilize product that is collected from the purification process so that any active impurity is deactivated before it can begin to form residue.

An additional purification step may include a pretreatment filtration through a polar medium such as silica gel or alumina in order to strip out impurities such as water, alcohols, peroxides, stabilizers, stabilizer degradation products, oxygenated organic impurities and particulate matter. This step is ideally used to condition raw material when charging a distillation flask. New, active stabilizer is added to the raw material, or the raw material is charged onto stabilizer in the flask, to replace any that was lost during the filtration process.

While distillation of cyclic alkenes may be carried out successfully at atmospheric pressure with minimal degradation, the purification process may be optimized for more sensitive cyclic alkenes by using alternative methods. As distillation at a reduced pressure lowers the boiling point of a cyclic alkene, those that are especially sensitive to heat can benefit from distillation at a reduced pressure. Alternatively, the use of short-path distillation equipment, such as a wiped-film or falling-film still, can reduce heated residence time and therefore reduce degradation that can lead to residue. Note that these methods reduce the effectiveness of separating out impurities that have a boiling point similar to the target cyclic alkene. Therefore, they may be used after an atmospheric distillation to strip out unwanted residual impurities that may have formed in the initial purification process.

Alternative methods of stabilizing a cyclic alkene may include: adding a stabilizer to a receiving vessel and running purified and unstabilized cyclic alkene onto the stabilizer, flowing purified and unstabilized cyclic alkene over a quantity of stabilizer as it passes to a receiving vessel in order to dissolve the stabilizer, and dosing stabilizer into purified and unstabilized cyclic alkene that has been collected in a receiving vessel.

Since most appropriate stabilizers are solids, they can be more difficult to manipulate and measure than liquids. Such stabilizers can be dissolved in appropriate liquid solvents, or they may even be dissolved in high concentration in the target cyclic alkene. An alternative method of stabilizing cyclic alkenes also includes dissolving a solid stabilizer in an appropriate liquid solvent or in a high concentration in the cyclic alkene, whereby the resulting liquid is then used to stabilize a cyclic alkene. Alternatively, several of the described stabilizers can also be melted and handled as a liquid to stabilize a cyclic alkene.

The methods of purification and stabilization of cyclic alkenes described above may be combined to ultimately provide a stabilized product with the highest purity while avoiding the potential to form impurities that can lead to residue.

Many chemical precursors and precursor compositions for the semiconductor industry are typically packaged, shipped and stored in stainless steel containers to retain product quality for the maximum amount of time. The product container is then connected to chemical delivery equipment that transfers the chemical by a precisely controlled means, to retain product and process purity and consistency. Such a process equipment is referred to here as a film deposition tool.

The compositions of the present disclosure may be used in any suitable chemical vapor deposition process which requires a cyclic alkene. Preferred processes are those chemical vapor deposition processes employing a silicon containing compound to deposit a low dielectric constant film. Examples of suitable processes include, but are not limited to those described in U.S. Pat. Nos. 6,815,373, 6,596,627, 6,756,323, 6,541,398, 6,479,110, 6,846,515, and 6,583,048, herein incorporated by reference.

This disclosure is also directed to a process of using a cyclic alkene composition for forming a layer of carbon-doped silicon oxide on a wafer. The process includes treating a cyclic alkene composition and a silicon containing compound in a film deposition chamber that contains a substrate, thereby forming a carbon doped silicon oxide film on the substrate. The process can further include, prior to the treatment step, providing the cyclic alkene composition in a first container, the silicon containing compound in a second container, a film deposition tool containing the film deposition chamber, a gas delivery line for connecting the first and second containers to the film deposition chamber within the film deposition tool, and a stream of carrier gas to sweep the cyclic alkene composition and the silicon containing compound through the gas delivery line into the film deposition chamber; introducing vapors of the cyclic alkene composition and the silicon containing compound into the carrier gas stream; and transporting the vapors of the cyclic alkene composition and silicon containing compound into the film deposition chamber via the carrier gas stream.

The cyclic alkenes suitable for the above-mentioned process can be the same as described previously (vide supra).

Silicon containing compounds suitable for this disclosure includes any class of silicon containing molecule such as silanes, alkylsilanes, alkoxysilanes, alkylalkoxysilanes, carboxysilanes, alkylcarboxysilanes, alkoxycarboxysilanes, alkylalkoxycarboxysilanes, linear siloxanes, cyclic siloxanes, fluorinated silanes, fluorinated alkylsilanes, fluorinated alkoxysilanes, fluorinated alkylalkoxysilanes, fluorinated carboxysilanes, fluorinated alkylcarboxysilanes, fluorinated alkoxycarboxysilanes, fluorinated alkylalkoxycarboxysilanes, fluorinated linear siloxanes, fluorinated cyclic siloxanes, and mixtures thereof. Examples of each class described above include, but are not limited to, those shown in Scheme 1 below. These silicon containing compounds may also be stabilized in a manner described by Teff et al. U.S. Pat. Nos. 7,129,311 and 7,531,590 using compounds of Formula (I), Formula (II) or mixtures thereof described therein.

Scheme 1

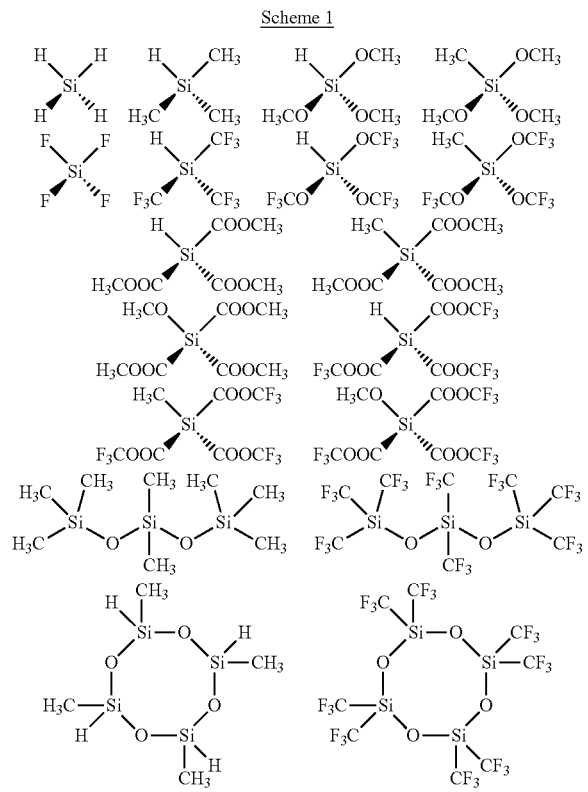

Suitable examples of silicon containing compounds of the present disclosure can also be those described by Formula (III):

(III)

In Formula (III), $R^{10}$ through $R^{13}$ can each independently be H, F, OH, $C_1$-$C_8$ linear alkyl, $C_3$-$C_8$ branched alkyl, $C_2$-$C_8$ unsaturated alkyl, $C_1$-$C_8$ linear alkoxy, $C_3$-$C_8$ branched alkoxy, $C_2$-$C_8$ unsaturated alkoxy, $C_4$-$C_8$ substituted cyclic alkyl or alkoxy, $C_3$-$C_8$ unsubstituted cyclic alkyl or alkoxy, substituted or unsubstituted aryl or aryl alkoxy, substituted silicon containing substituent, partially or fully fluorinated $C_1$-$C_8$ linear alkyl, $C_3$-$C_8$ branched alkyl, $C_2$-$C_8$ unsaturated alkyl, partially or fully fluorinated $C_1$-$C_8$ linear alkoxy, $C_3$-$C_8$ branched alkoxy, $C_2$-$C_8$ unsaturated alkoxy, partially or fully fluorinated $C_4$-$C_8$ substituted cyclic alkyl or alkoxy, $C_3$-$C_8$ unsubstituted cyclic alkyl or alkoxy, partially or fully fluorinated substituted or unsubstituted aryl or aryl alkoxy, partially or fully fluorinated substituted silicon containing substituent, non-, partially or fully fluorinated carboxylate ligands, or mixtures thereof. Examples of $R^{10}$ through $R^{13}$ in Formula (III) include, but are not limited to, H, F, OH, methyl, ethyl, propyl, iso-propyl, iso-propenyl, butyl, phenyl, methylphenyl, cyclohexyl, methylcyclohexyl, methoxy, ethoxy, propoxy, iso-propoxy, butoxy, phenoxy, methylphenoxy, cyclohexyloxy, methylcyclohexyloxy, trifluoromethyl, trifluoroethyl, penatafluoroethyl, trifluoropropyl, pentafluoropropyl, heptafluoropropyl, isopropyl, hexafluoroisopropyl, trifluoroisopropenyl, trifluorobutyl, pentafluorobutyl, nonafluorobutyl, trifluorophenyl, (trifluoromethyl)tetrafluorophenyl, undecafluorocyclohexyl, (trifluoromethyl)decafluorocyclohexyl, trifluoromethoxy, trifluoroethoxy, pentafluoroethoxy, trifluoropropoxy, pentafluoropropoxy, heptafluoropropoxy, hexafluoroisopropoxy, heptafluoroisopropoxy, trifluorobutoxy, pentafluorobutoxy, nonafluorobutoxy, pentafluorophenoxy, (trifluoromethyl)tetrafluorophenoxy, undecafluorocyclohexyloxy, (trifluoromethyl) decafluorocyclohexyloxy, dimethylsiloxy (in the case of linear siloxanes), trimethylsiloxy, trimethyldisiloxy, pentamethyldisiloxy, diethylsiloxy, triethylsiloxy, triethyldisiloxy, pentaethyldisiloxy, dimethoxysiloxy, trimethoxysiloxy, trimethoxydisiloxy, pentamethoxydisiloxy, diethoxysiloxy, triethoxysiloxy, triethoxydisiloxy, pentaethoxydisiloxy, $\eta^2$-trimethyltrisiloxy (in the case of cyclic siloxanes, such as tetramethylcyclotetrasiloxane) and $\eta^2$-hexamethyltrisiloxy (in the case of cyclic siloxanes, such as octamethylcyclotetrasiloxane). Preferred examples of $R^{10}$ through $R^{13}$ include H, F, methyl, methoxy, ethyl, ethoxy and siloxy. For Formula (III), H, methyl, ethoxy and substituted siloxy are most preferred for $R^{10}$ through $R^{13}$ for use in semiconductor applications.

Examples of silicon containing compounds suitable for this disclosure include, but are not limited to, silane, methylsilane, dimethylsilane, trimethylsilane, tetramethylsilane, ethylsilane, diethylsilane, triethylsilane, tetraethylsilane, propylsilane, dipropylsilane, tripropylsilane, tetrapropylsilane, isopropylsilane, diisopropylsilane, triisopropylsilane, tetraisopropylsilane, butylsilane, dibutylsilane, tributylsilane, tetrabutylsilane, methyltrimethoxysilane, dimethyldimethoxysilane, trimethylmethoxysilane, trimethoxysilane, tetramethoxysilane, methylmethoxysilane, methyldimethoxysilane, methyltriethoxysilane, dimethyldiethoxysilane, trimethylmethoxysilane, tetraethoxysilane, methylethoxysilane, methyldiethoxysilane, methylpropoxysilane, dimethyldipropoxysilane, trimethylpropoxysilane, tetrapropoxysilane, methyltriisopropoxysilane, dimethyldiisopropoxysilane, trimethylisopropoxysilane, tetraisopropoxysilane, methyldiisopropoxysilane, methylphenylsilane, methyldiphenylsilane, methyltriphenylsilane, dimethyldiphenylsilane, trimethylphenylsilane, methyl(methylphenyl)silane, methyldi(methylphenyl)silane, methyltri(methylphenyl)silane, methylphenoxysilane, methyldiphenoxysilane, dimethyldiphenoxysilane, methyl(methylphenoxy)silane, methyldi(methylphenoxy)silane, dimethyldi(methylphenoxy)silane, methyl(cyclohexyl)silane, methyldi(cyclohexyl)silane, methyltri(cyclohexyl)silane, dimethyldi(cyclohexyl)silane, trimethyl(cyclohexyl)silane, methyl(methylcyclohexyl)silane, methyldi(methylcyclohexyl)silane, methyltri(methylcyclohexyl)silane, dimethyldi(methylcyclohexyl)silane, trimethyl(methylcyclohexyl)silane, methyl(cyclohexyloxy)silane, methyldi(cyclohexyloxy)silane, methyl(tricyclohexyloxy)silane, dimethyldi(cyclohexyloxy)silane, methyl(methylcyclohexyloxy)silane, methyldi(methylcyclohexyloxy)silane, methyltri(methylcyclohexyloxy)silane, dimethyldi(methylcyclohexyloxy)silane, silicon tetrafluoride, fluorotrimethylsilane, methyltris(trifluoromethoxy)silane, trifluoromethyltris(trifluoromethoxy)silane, fluorotriethoxysilane, triacetoxysilane, methoxytriacetoxysilane, vinyltriacetoxysilane, vinylmethyldiacetoxysilane, trimethylsilyl(trimethylsilyl)propynoate, trimethylsilyl(trimethylsiloxy)acetate, trimethylsilyltrifluoroacetate, tris(trifluoromethylsilyl)trifluoroacetate, triethylacetoxysilane, tri(trifluoroacetoxy)silane, methyltri(trifluoroacetoxy)silane, methoxytri(trifluoroacetoxy)silane, tetra(trifluoroacetoxy)silane, tetraacetoxysilane, phenyltriacetoxysilane, phenyldimethylacetoxysilane, phenyldimethoxyacetoxysilane, phenylacetoxytrimethylsilane, 1,1,1,3,3-pentamethyl-3-acetoxydisiloxane, methyltriacetoxysilaneethyltriacetoxysilane, methyltriacetoxysilane, methacryloxytrimethylsilane, ethyltriacetoxysilane, dimethyldiacetoxysilane, di-t-butoxydiacetoxysilane, dibenzyloxydiacetoxysilane, bis(trimethylsilyl)malonate, bis(trimethylsilyl)acetylenedicarboxylate, acryloxytrimethylsilane, acetoxytrimethylsilane, acetoxymethyldimethylacetoxysilane, triethyl(trifluoroacetoxy)silane, phenyltri(trifluoroacetoxy)silane, phenyldi(trifluoromethyl)acetoxysilane, (pentafluorophenyl)dimethylacetoxysilane, phenyldimethyl(trifluoroacetoxy)silane, phenyl(trifluoroacetoxy)trimethylsilane, (trifluorophenyl)acetoxytrimethylsilane, phenylacetoxytri(trifluoromethyl)silane 1,1,1,3,3-penta(trifluoromethyl)-3-acetoxydisiloxane, (trifluoromethyl)triacetoxysilaneethyltriacetoxysilane, (trifluoromethyl)triacetoxysilane, (trifluoromethyl)(trifluoromethoxy)diacetoxysilane, methacryloxytri(trifluoromethyl)silane, (trifluoroethyl)triacetoxysilane, di(trifluoromethyl)diacetoxysilane, di-(nonafluoro-t-butoxy)diacetoxysilane, dibenzyloxydi(trifluoroacetoxy)silane, acryloxytri(trifluoromethyl)silane, acetoxytri(trifluoromethyl)silane, acetoxy(trifluoromethyl)dimethylacetoxysilane, (trifluoromethyl)silane, di(trifluoromethyl)silane, tri(trifluoromethyl)silane, tetra(trifluoromethyl)silane, (trifluoroethyl)silane, di(trifluoroethyl)silane, tri(trifluoroethyl)silane, tetra(trifluoroethyl)silane, (trifluoropropyl)silane, di(trifluoropropyl)silane, tri(trifluoropropyl)silane, tetra(trifluoropropyl)silane, (hexafluoroisopropyl)silane, di(hexafluoroisopropyl)silane, tri(hexafluoroisopropyl)silane, tetra(hexafluoroisopropyl)silane, (trifluorobutyl)silane, di(trifluorobutyl)silane, tri(trifluorobutyl)silane, tetra(trifluorobutyl)silane, (trifluoromethyl)trimethoxysilane, di(trifluoromethyl)dimethoxysilane, tri(trifluoromethyl)methoxysilane, tetra(trifluoromethoxy)silane, (trifluoromethyl)methoxysilane, (trifluoromethyl)dimethoxysilane, (trifluoromethyl)triethoxysilane, di(trifluoromethyl)diethoxysilane, tri(trifluoromethyl)methoxysilane, tetra(trifluoroethoxy)silane, (trifluoromethyl)ethoxysilane, (trifluoromethyl)diethoxysilane, (trifluoromethyl)propoxysilane, di(trifluoromethyl)dipropoxysilane, tri(trifluoromethyl)propoxysilane, tetra(trifluoropropoxy)silane, (trifluoromethyl)triisopropoxysilane, di(trifluoromethyl)diisopropoxysilane, tri(trifluoromethyl)isopropoxysilane, tetra(trifluoroisopropoxy)silane, (trifluoromethyl)diisopropoxysilane, (trifluoromethyl)phenylsilane, (trifluoromethyl)diphenylsilane, (trifluoromethyl)triphenylsilane, di(trifluoromethyl)diphenylsilane, tri(trifluoromethyl)phenylsilane, (trifluoromethyl)(methylphenyl)silane, (trifluoromethyl)di(methylphenyl)silane, (trifluoromethyl)tri(methylphenyl)silane, (trifluoromethyl)phenoxysilane, (trifluoromethyl)diphenoxysilane, di(trifluoromethyl)diphenoxysilane, (trifluoromethyl)(methylphenoxy)silane, (trifluoromethyl)di(methylphenoxy)silane, di(trifluoromethyl)di(methylphenoxy)silane, (trifluoromethyl)(cyclohexyl)silane, (trifluoromethyl)di(cyclohexyl)silane, (trifluoromethyl)tri(cyclohexyl)silane, di(trifluoromethyl)di(cyclohexyl)silane, tri(trifluoromethyl)(cyclohexyl)silane, (trifluoromethyl)(methylcyclohexyl)silane, (trifluoromethyl)di(methylcyclohexyl)silane, (trifluoromethyl)tri(methylcyclohexyl)silane, di(trifluoromethyl)di(methylcyclohexyl)silane, tri(trifluoromethyl)(methylcyclohexyl)silane, (trifluoromethyl)(cyclohexyloxy)silane, (trifluoromethyl)di(cyclohexyloxy)silane, (trifluoromethyl)tri(cyclohexyloxy)silane, di(trifluoromethyl)di(cyclohexyloxy)silane, (trifluoromethyl)(methylcyclohexyloxy)silane, (trifluoromethyl)di(methylcyclohexyloxy)silane, (trifluoromethyl)tri(methylcyclohexyloxy)silane, di(trifluoromethyl)di(methylcyclohexyloxy)silane, tri(trifluoromethoxy)silane, methyltri(trifluoromethoxy)silane, dimethyldi(trifluoromethoxy)silane, trimethyl(trifluoromethoxy)silane, methyl(trifluormethoxy)silane, methyldi(trifluoromethoxy)silane, methyltri(trifluoroethoxy)silane, dimethyldi(trifluoroethoxy)silane, trimethyl(trifluoromethoxy)silane, methyl(trifluoroethoxy)silane, methyldi(trifluoroethoxy)silane, methyl(trifluoropropoxy)silane, dimethyldi(trifluoropropoxy)silane, trimethyl(trifluoropropoxy)silane, methyltri(hexafluoroisopropoxy)silane, dimethyldi(hexafluoroisopropoxy)silane, trimethyl(hexafluoroisopropoxy)silane, methyldi(hexafluoroisopropoxy)silane, methyl(pentafluorophenyl)silane, methyldi(pentaphenyl)silane, methyltri(pentaphenyl)silane, dimethyl(pentafluorophenyl)silane, trimethyl(pentafluorophenyl)silane, methyl[(trifluoromethyl)phenyl]silane, methyldi[(trifluoromethyl)phenyl]silane, methyltri[(trifluoromethyl)phenyl]silane, methyl(pentafluorophenoxy)silane, methyldi(pentafluorophenoxy)silane, dimethyldi(pentafluorophenoxy)silane, methyl[(trifluoromethyl)phenoxy]silane, methyldi[(trifluoromethyl)phenoxy]silane, dimethyldi[(trifluoromethyl)phenoxy]silane, methyl(undecafluorocyclohexyl)silane, methyldi(undecafluorocyclohexyl)silane, methyltri(undecafluorocyclohexyl)silane, dimethyldi(undecafluorocyclohexyl)silane, trimethyl(undecacyclohexyl)silane, methyl[(trifluoromethyl)cyclohexyl]silane, methyldi[(trifluoromethyl)cyclohexyl]silane, methyltri[(trifluoromethyl)cyclohexyl]silane, dimethyldi[(trifluoromethyl)cyclohexyl]silane, trimethyl[(trifluoromethyl)cyclohexyl]silane, methyl(undecafluorocyclohexyloxy)silane, methyldi(undecafluorocyclohexyloxy)silane, methyltri(undecafluorocyclohexyloxy)silane, dimethyldi(undecafluorocyclohexyloxy)silane, methyl[(trifluoromethyl)cyclohexyloxy]silane, methyldi[(trifluoromethyl)cyclohexyloxy]silane, methyltri[(trifluoromethyl)cyclohexyloxy]silane, dimethyldi[(trifluoromethyl)cyclohexyloxy]silane, hexamethyldisiloxane, octamethyltrisiloxane, octa(trifluoromethyl)trisiloxane, trimethyltrisiloxane, diethyltrimethyltrisiloxane, trimethylcyclotrisiloxane, tetramethylcyclotetrasiloxane, pentamethylcyclopentasiloxane, tetraethylcyclotetrasiloxane, pentaethylcyclopentasiloxane, hexamethylcyclotrisiloxane, octamethylcyclotetrasiloxane, decamethylcyclopentasiloxane, vinylmethyldiethoxysilane vinylmethyldimethoxysilane, trimethylsilylacetylene, di(trimethylsilyl)acetylene, hexa(trifluoromethyl)disiloxane, octa(trifluoromethyl)trisiloxane, tris(trifluoromethyl)trisiloxane, tris(trifluoromethyl)cyclotrisiloxane, tetra(trifluoromethyl)cyclotetrasiloxane, octa(trifluoromethyl)cyclotetrasiloxane and mixtures thereof.

Preferred examples of silicon containing compounds in Formula (III) include trimethylcyclotrisiloxane, triethylcyclotrisiloxane, tetramethylcyclotetrasiloxane, tetraethylcyclotetrasiloxane, pentamethylcyclopentasiloxane, pentaethylcyclopentasiloxane, octamethylcyclotetrasiloxane, methyltriethoxysilane, vinylmethyldimethoxysilane, vinylmethyldiethoxysilane, trimethylsilylacetylene, bis(trimethylsilyl)acetylene, methyldimethoxysilane and methyldiethoxsilane. Tetramethylcyclotetrasiloxane, methyldiethoxysilane, dimethyldimethoxysilane and trimethylsilylacetylene are most preferred for use in the semiconductor industry.

Figure 2:
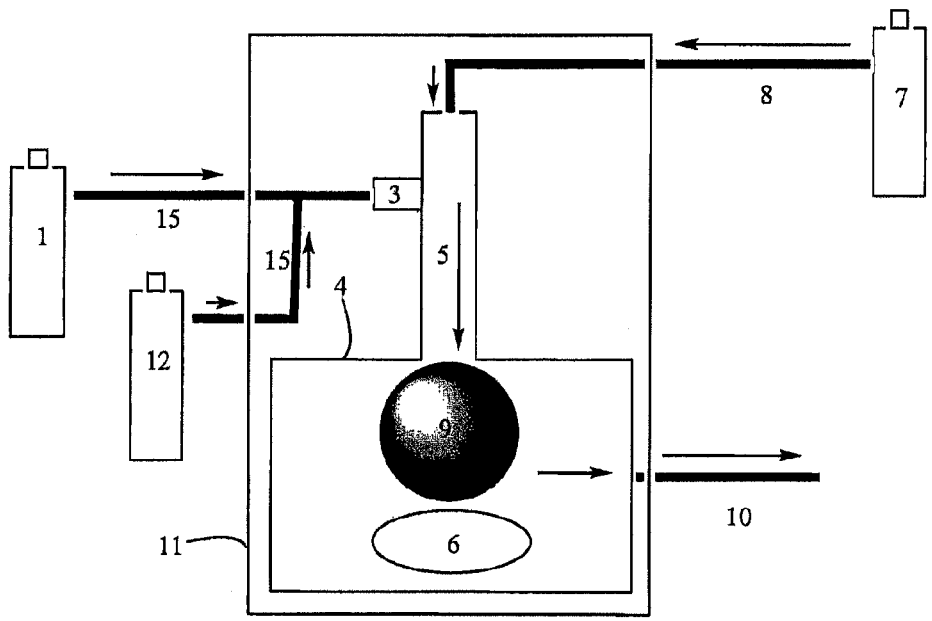
FIG. 2 is a representation of a film deposition tool used in the semiconductor industry for use with the compositions according to this disclosure, where a single vaporizer means is used with two separate precursors.

In a typical chemical vapor deposition process requiring at least two precursors, there are several methods by which the components can be combined. Such a process is shown in FIGS. 1 and 2. For example, one precursor (e.g., a cyclic alkene) is transported from a container (1), through chemical delivery lines (2), to a vaporizer means (3) housed in the film deposition tool (11). The precursor can be transported from the container (1) through the delivery line (2) to the vaporizer means (3) by a variety of means, including, but not limited to, pressurization of the container with an inert gas, use of a mechanical pumping mechanism, gravity feed, or combinations thereof. The second precursor (e.g., a silicon containing compound) is transported from a separate container (12), through chemical delivery lines (13), to a vaporizer means (14) housed in the film deposition tool (11). The second precursor can be transported from the container (12) through the delivery line (13) to the vaporizer means (14) by a variety of means, including, but not limited to, pressurization of the container with an inert gas, use of a mechanical pumping mechanism, gravity feed, or combinations thereof.

In the event that the second precursor (e.g., a silicon containing compound) is a gas at room temperature, or it requires substantially little or no energy to be vaporized as it is introduced into the chemical vapor process line (5), a second vaporizer means (14) may be replaced by a valve, check valve, baffle, diffusing apparatus or similar device meant to infuse gas into a tube or chamber without a means to enable vaporization.

It is important to note that, while it is desirable to have at least one vaporizer means (3) attached to a chemical vapor process line (5), it is also possible to connect at least one vaporizer means (3) directly to the deposition chamber (4), optionally connecting one or more additional vaporizer means (14) to a chemical vapor process line (5) or directly to the deposition chamber (4). Additionally, a gas delivery line (8) may optionally be connected directly to the deposition chamber (4). In the event that no vaporizer means (3, 14) or gas delivery lines (8) are connected to a chemical vapor process line (5), the chemical vapor process line becomes a feature that is optionally attached to the deposition chamber (4).

Ideally, separate chemical delivery lines and vaporizer means are used for each precursor. However, it is possible for two precursors to be vaporized using a single vaporizer means when the two precursors are chemically compatible. When using a single vaporizer means (3), both precursors are combined or separately dispensed through a portion of the chemical delivery line (15) to the vaporizer means (3). When the two precursors are combined prior to vaporization, as shown in FIG. 2, the process simply involves their combination in the chemical delivery line (15), followed by vaporization of the two precursors in the vaporizer means (3). When the two precursors are separately dispensed through a single vaporizer means (3), the sequence to dispense each precursor could simply involve flow of one precursor through the chemical delivery line (15) to the vaporizer means (3) followed by flow of a second precursor through the chemical delivery line (15) to the vaporizer means (3) without repetition. Alternatively, there may be a need to flow one precursor, flow the second precursor, and repeat these steps until the desired layer is formed. The process used is wholly dependent on the film properties desired. In the event that only one vaporizer means (3) is used, the second vaporizer means (14) is not needed.

In a process of flowing two different precursors through separate chemical lines and vaporizer means, a suitable precursor flow rate for each precursor can range from about 0.01 to about 10 mL/minute. The vaporizer means (3, 14) serves as a means to convert liquid precursor to a vapor or mist, and it can use various techniques, such as heat, high pressure gas, or other means to accomplish this task. Alternatively, the vaporizer means (3, 14) may consist of a container that holds a volume of liquid, through which an inert gas is flowed as a means to (a) convert the precursor from a liquid to a vapor, and (b) transport the precursor vapor into the chemical vapor process line (5). Regardless of the vaporizer means (3, 14) design, the conversion of the precursor from liquid to gaseous state may take place either in the vaporizer means (3, 14) or in the chemical vapor process line (5). The precursor is injected in the form of a vapor or mist into the chemical vapor process line (5) that is commonly heated between about 30° C. and about 120° C. to prevent the precursor vapor from condensing inside the line (5). Mixing of the precursor components can take place in the chemical vapor process line (5), or in different locations within the deposition chamber (4), depending on where the vaporizer means (3, 14) are located with respect to one another. The chemical vapor process line (5) is connected to the deposition chamber (4) inside the film deposition tool (11), and substrate (6) is housed within the deposition chamber (4). The deposition chamber (4) and chemical vapor process line (5) may be operated at ambient pressure (i.e., 760 torr), but it is also common to operate below atmospheric pressure, from about 0.01 torr to about 700 torr, to enhance vaporization of the precursors and to help keep the precursors in the vapor phase.

It should be understood by those skilled in the art that the connection between the chemical vapor process line (5) and the deposition process chamber (4) can vary from deposition tool to deposition tool, depending on the requirements for the process. For example, designs may include various apparatuses that affect the mixing, heating, cooling, or distribution of gases within the system. These may include an apparatus having baffles to mix the gases, a heated zone to heat gases, a cooling zone to cool gases, a chamber to allow pressure equilibration, or a showerhead to distribute gases over the surface of a wafer. Designs may, for example, route chemical vapors from the chemical vapor process line (5) through a baffled mixing apparatus, through a heated zone and through a showerhead before the gases are passed to the substrate (6) in the deposition chamber (4). Due to the complexity of designs that are available in the market and their variability based on need driven by the process, the options are described only in general terms here.

In our general example, the precursor vapors are transported through the chemical vapor process line (5) to the substrate (6) in the deposition chamber (4) by a stream of gas flowing past the vaporizer means (3, 14). The stream of gas is supplied from a source tank (7) and flows through a gas delivery line (8) to the chemical vapor process line (5). The stream of gas, having a flow rate of about 5 sccm to about 10,000 sccm, is often heated to enhance vaporization of the precursors to help keep the precursors in the vapor phase. The gas used may be inert, such as nitrogen, helium or argon, chosen simply to act as a means to transport the precursor vapor to the substrate, or it may be a reactive gas, such as oxygen, ozone, ammonia, nitrous oxide, carbon dioxide, carbon monoxide, $SiH_4$, silanes, silicon tetrafluoride, hydrazine and the like to enhance the deposition process.

As the precursor vapors are transported to the substrate (6), they may be mixed with one or more reactants, in addition to the transport gas, to enhance its deposition onto the substrate. The reactants may be reactive gases as mentioned above, or they may be other chemical precursors such as amines, aminoalcohols, alkanes, alkenes, alkynes, alcohols, esters, ketones, aldehydes, carboxylic acids and the like. The reactants are carefully selected to enhance the deposition of precursor on the substrate, and to modify the chemical identity and properties of the layer deposited onto the substrate. These reactants can be introduced into the film deposition tool (11) by various means and at various locations in the process, depending on the desired effect. It is most convenient to introduce a reactant into the film deposition tool (11) in gaseous form, so it would be necessary to have an additional vaporizer means in the case where liquid reactants are used. An additional vaporizer means, or gas delivery line used to introduce a reactant can be placed near the point where the gas delivery line (8) meets the chemical vapor process line (5), upstream or downstream of the vaporizer means, directly into or near the plasma (9), and/or somewhere on the sides, top, or bottom of the film deposition chamber (4) of the film deposition tool (11).

The precursor vapors, potential reactants, and inert or reactive gases may also experience other conditions used to enhance deposition, such as heat or plasma (9). The precursor vapor may be preheated to between about 50° C. and about 800° C. before contact with the substrate to enhance the deposition of the precursors on the substrate. A plasma may also be used to add energy to the precursor vapors and enhance the deposition. Additionally, the plasma may be pulsed on and off to change the properties of the deposited film. The plasma power and pulse duration are carefully selected to enhance the deposition of the precursors on the substrate, and to modify the chemical identity and properties of the layer deposited onto the substrate. The plasma may also be applied over a range of frequencies, where the high and low frequency plasma power may range from about 0 to several kilowatts. The substrate may also have a bias of between about 0 and about −400 VDC to enhance material transport to the substrate. The substrate may be heated from about 25° C. to about 500° C. to either cause thermal breakdown of the precursor on the substrate, or may be used to enhance the deposition of precursor on the substrate. Unreacted materials are exhausted through an exhaust line (10).

The elemental composition of the film, and thus the film properties, can be adjusted by the choice of starting silicon containing compound, the cyclic alkene employed, and the use or lack of use of various reactive gases in the process.

Subsequent to the film deposition, the initial film may be subjected to a curing step. The curing steps may also be employed to modify e.g., the density or elemental compositions of the films to change film properties such as film strength, dielectric constant and various other properties of the film. These curing steps may include a thermal treatment by the application of heat through one of various heating means such as hot plates, ovens, infrared lamps, or microwaves. Alternatively, the curing may include a plasma treatment, or a chemical treatment of the film. These curing steps may take place in an inert atmosphere (e.g., noble gases), a reducing atmosphere (e.g., hydrogen or hydrocarbon), or an oxidizing atmosphere (e.g., oxygen, air, ozone, nitrous oxide, carbon dioxide) depending on the desired chemical change in the initial film. Such processes are known to those skilled in the art.

EXAMPLES

A series of tests were devised to compare the propensity for stabilized and unstabilized NBDE samples to form soluble, nonvolatile polymeric residue under various stress conditions. In these tests, samples were prepared by carefully distilling NBDE under nitrogen using similar conditions. For stabilized samples, NBDE was distilled under nitrogen directly onto each stabilizer. After the samples were prepared, they were transferred into 250 mL glass bulb test containers that were fitted with a Kontes valve and Schlenk line adapter. This container was ideal for testing since it could be resealed, was compatible with Schlenk techniques, and the only wetted parts were glass or Teflon. The samples were carefully handled under nitrogen to prevent exposure to adventitious gases before the experiment. Some samples were degassed using three freeze-pump-thaw cycles to remove dissolved gases. Some samples were exposed to oxygen, where the amount of oxygen was carefully introduced using calculated amounts of air. All heated samples were heated in a controlled temperature oil bath for a specific length of time. After each experiment was completed, the amount of nonvolatile, polymeric residue was determined using an evaporative technique that separated the volatile portion (NBDE and stabilizer) from the nonvolatile portion (polymeric residue). The evaporative technique simultaneously evaporated NBDE and stabilizer from a preweighed sample pan inside a container fitted with a nitrogen inlet and a vapor outlet. Nitrogen flow and heating at 80° C. facilitated the evaporation process, and residue was determined by the difference in the weight of the sample pan before and after the test. The amount of residue was reported as parts per million (ppm) by weight after comparing the mass of the nonvolatile portion to the total weight of the sample, and the detection limit was approximately 0.5 ppm. Lower residue values after testing are an indication of greater stability.

Example 1

This test was chosen to demonstrate how NBDE performs when exposed to heat for a period of time. As mentioned previously, NBDE may be exposed to elevated temperatures up to 80° C. for hours or days, so the product must demonstrate resistance to thermal degradation under such conditions.

Additionally, this test can give an initial indication of product shelf life. Accelerated aging tests commonly assume that chemical reactions follow the Arrhenius reaction rate function. Generally, this states that degradation rates increase 2× with every 10° C. increase in temperature. Therefore, a heating test at 80° C. for 8.1 days is approximately equal to a sample stored at 25° C. for 365 days. For the above test, 80° C. for 12 hours is approximately equal to a sample stored at 25° C. for 3 weeks.

The stabilizers tested were MHQ and 4-MCAT, and each was tested at two different concentrations to determine if a higher concentration was more effective. The initial residue concentration for each sample was measured to determine the baseline prior to heating. The baselines were 31 ppm for unstabilized NBDE (Sample 1), lower than 2 ppm for Samples 2-3, and lower than 0.5 ppm for Samples 4-5. Since all distillations were done under the same conditions, this could be an indication of the difficulty of isolating high purity NBDE in the absence of a stabilizer. Once the baseline was established, sample bulbs were carefully filled in the absence of air and subsequently degassed as described above. The samples were heated at 80° C. for 12 hours and then tested for residue concentration. The test results are summarized in Table 1 below.

TABLE 1

Stability Tests of Degassed NBDE at 80° C.

| Sample | Time (hr) | T (° C.) | Reactive Gas | Stabilizer | Type | Residue (ppm) |
|---|---|---|---|---|---|---|
| 1 | 12 | 80 | Degassed | None | N/A | 227 |
| 2 | 12 | 80 | Degassed | 50 ppm MHQ | Monohydroxy | 122 |
| 3 | 12 | 80 | Degassed | 100 ppm MHQ | Monohydroxy | 83 |
| 4 | 12 | 80 | Degassed | 50 ppm 4-MCAT | Dihydroxy | <0.5 |
| 5 | 12 | 80 | Degassed | 100 ppm 4-MCAT | Dihydroxy | <0.5 |

Results in Table 1 show that the unstabilized sample formed a fair amount of residue. Comparing the monohydroxybenzene stabilized samples to unstabilized material, MHQ showed a reduction in residue. The higher concentration of MHQ gave a lower residue concentration. However, the dihydroxybenzene stabilized samples both unexpectedly showed improved performance over each of the monohydroxybenzene stabilized samples, with excellent results at either concentration.

Example 2

This test was chosen to demonstrate how NBDE performs when exposed to both heat and oxygen for certain lengths of time. The oxygen concentration used for this test was 25 ppm by weight. This concentration is similar to what one would expect from an accidental exposure of chemical to air during packaging, though it is a relatively large exposure considering the lengths usually taken by chemical manufacturers to avoid oxygen contamination when preparing semiconductor grade products.

The stabilizers tested were MHQ and 4-MCAT, and each was tested at two different concentrations to determine if a higher concentration was more effective. The initial residue concentration for each sample was measured to determine the baseline prior to heating. The baselines were 31 ppm for unstabilized NBDE (Sample 6), lower than 2 ppm for Samples 7-8 were, and lower than 0.5 ppm for Samples 9-10. Once the baseline was established, sample bulbs were filled in the presence of a known quantity of air to give 25 ppm of oxygen by weight of the sample. The samples were heated at 80° C. for 12 hours and then tested for residue concentration. The results are summarized in Table 2 below.

TABLE 2

Stability Tests of NBDE with 25 ppm $O_2$ at 80° C.

| Sample | Time (hr) | T (° C.) | Gas | Reactive Stabilizer | Type | Residue (ppm) |
|---|---|---|---|---|---|---|
| 6 | 12 | 80 | 25 ppm $O_2$ | None | N/A | 1588 |
| 7 | 12 | 80 | 25 ppm $O_2$ | 50 ppm MHQ | Monohydroxy | 836 |
| 8 | 12 | 80 | 25 ppm $O_2$ | 100 ppm MHQ | Monohydroxy | 576 |
| 9 | 12 | 80 | 25 ppm $O_2$ | 50 ppm 4-MCAT | Dihydroxy | 3 |
| 10 | 12 | 80 | 25 ppm $O_2$ | 100 ppm 4-MCAT | Dihydroxy | <0.5 |

Results in Table 2 show that the unstabilized sample formed a significant amount of residue. Comparing the monohydroxy stabilized samples to unstabilized material, MHQ showed a reduction in residue. The higher concentration of MHQ gave a lower residue concentration. However, the dihydroxybenzene stabilized samples both unexpectedly showed improved performance over each of the monohydroxybenzene stabilized samples. Though there were excellent results at either concentration, the higher stabilizer concentration showed better performance.

Example 3

This test was chosen as an extreme condition to stress the product and help sort out the effectiveness of different stabilizers. Oxygen was added at 150 ppm by weight as a way to stress the product and demonstrate clear differences between more and less effective stabilizers.

The stabilizers tested are as follows: 4-methoxyphenol (MHQ), 2,6-di-tert-butyl-4-methylphenol (BHT), 2,6-di-tert-butyl-4-methoxyphenol (BHA), 3-methoxy-1,2-dihydroxybenzene (3-MOCAT), 4-methyl-1,2-dihydroxybenzene (4-MCAT) and 1,2-dihydroxybenzene (pyrocatechol). The first three stabilizers have a single OH substituent (monohydroxy) while the last three have two OH substituents (dihydroxy). The initial residue concentration for each sample was measured to determine the baseline prior to heating. The baselines were 31 ppm for unstabilized NBDE (Sample 11) and lower than 2 ppm for Samples 12-17. Once the baseline was established, sample bulbs were filled in the presence of a known quantity of air to give 150 ppm of oxygen by weight of the sample. The samples were heated at 80° C. for 12 hours and then tested for residue concentration. The results are summarized in Table 3.

TABLE 3

Stability Tests of NBDE with 150 ppm $O_2$ at 80° C.

| Sample | Time (hr) | T (° C.) | Reactive Gas | Stabilizer | Type | Residue (ppm) |
|---|---|---|---|---|---|---|
| 11 | 12 | 80 | 150 ppm $O_2$ | None | N/A | 10487 |
| 12 | 12 | 80 | 150 ppm $O_2$ | 150 ppm MHQ | Monohydroxy | 1800 |

TABLE 3-continued

Stability Tests of NBDE with 150 ppm $O_2$ at 80° C.

| Sample | Time (hr) | T (° C.) | Reactive Gas | Stabilizer | Type | Residue (ppm) |
|---|---|---|---|---|---|---|
| 13 | 12 | 80 | 150 ppm $O_2$ | 150 ppm BHT + 50 ppm MHQ | Monohydroxy | 45 |
| 14 | 12 | 80 | 150 ppm $O_2$ | 150 ppm BHA + 50 ppm MHQ | Monohydroxy | 38 |
| 15 | 12 | 80 | 150 ppm $O_2$ | 150 ppm 3-MOCAT | Dihydroxy | 16 |
| 16 | 12 | 80 | 150 ppm $O_2$ | 150 ppm 4-MCAT | Dihydroxy | 11 |
| 17 | 12 | 80 | 150 ppm $O_2$ | 150 ppm pyrocatechol | Dihydroxy | 7 |

Results in Table 3 show that the unstabilized sample formed a significant amount of residue compared to all of the stabilized samples. This result was notably higher than tests performed in Examples 1 and 2 which used milder conditions. Samples 13 and 14 were prepared to probe the effectiveness of stabilizer mixtures. Comparing the monohydroxybenzene stabilized samples to unstabilized material, MHQ showed a marked reduction in residue but the MHQ mixtures with BHT or BHA both performed better. However, the dihydroxybenzene stabilized samples showed improved performance over each of the monohydroxybenzene stabilized samples at an equivalent or lower concentration.

Example 4

This test was chosen to demonstrate how a product would perform when exposed to a greater heat extreme for a period of time. Although NBDE is not expected to experience temperatures of 120° C. for 24 hours, is test can demonstrate if this extreme temperature adversely affects the product. It may also give an initial indication of shelf life where 24 hours at 120° C. is approximately equal to 2 years at 25° C.

The stabilizers tested were MHQ and 4-MCAT, and each was tested at two different concentrations to determine if a higher concentration was more effective. The initial residue concentration for each sample was measured to determine the baseline prior to heating. The baseline was 31 ppm for unstabilized NBDE (Sample 18), lower than 2 ppm for Samples 19-20, and lower than 0.5 ppm for Samples 21-22. Once the baseline was established, sample bulbs were carefully filled in the absence of air and subsequently degassed as described above. The samples were heated at 120° C. for 24 hours and then tested for residue concentration. The results are summarized in Table 4.

TABLE 4

Stability Tests of NBDE without $O_2$ at 120° C.

| Sample | Time (hr) | T (° C.) | Reactive Gas | Stabilizer | Type | Residue (ppm) |
|---|---|---|---|---|---|---|
| 18 | 24 | 120 | Degassed | None | N/A | 1862 |
| 19 | 24 | 120 | Degassed | 50 ppm MHQ | Monohydroxy | 822 |
| 20 | 24 | 120 | Degassed | 100 ppm MHQ | Monohydroxy | 331 |
| 21 | 24 | 120 | Degassed | 50 ppm 4-MCAT | Dihydroxy | 157 |
| 22 | 24 | 120 | Degassed | 100 ppm 4-MCAT | Dihydroxy | 157 |

Results in Table 4 show that the unstabilized sample formed significant residue. While the amount of residue formed was greater than that seen at 80° C. when degassed (see Table 1), not as much residue was formed compared to that formed when the unstabilized sample was exposed to both heat and oxygen (see Table 3). Comparing the monohydroxybenzene stabilized samples to unstabilized material, MHQ showed a reduction in residue. Further, the higher concentration of MHQ gave a lower residue concentration. However, the dihydroxybenzene stabilized samples both unexpectedly showed improved performance over each of the monohydroxybenzene stabilized samples at either concentration, even at this extreme temperature.

It is important to note that all samples of this Example showed evidence of thermal degradation as detected by gas chromatography-mass spectrometry (GC-MS) and the resulting residue had a different appearance. Residue formed in the presence of oxygen gave colorless or white yellow solid (often a "bubbly" mass) while residue formed at 120° C. gave a tan colored solid with the appearance of melted caramel. Since a phenolic stabilizer may not necessarily be effective against thermal degradation (e.g., due to a Diels-Alder 2+2 addition), this test may not be a reliable way to gauge the effectiveness of such stabilizers. Since there appear to be two active modes of degradation at 120° C., it is not possible to rely on the Arrhenius model to predict shelf life testing at this temperature.

Example 5

The cyclic alkene, NBDE, stabilized with 100 ppm of 4-MCAT or 3-MOCAT is transferred, with the aid of helium pressure, from a stainless steel container through a chemical delivery line to a heated vaporizer at a flow rate of 1 mL/min. The cyclic alkene is vaporized into a chemical vapor process line that is heated to 80° C. and transported to a substrate using 500 sccm of helium as a transport gas with the system base pressure held at 6 torr. During transport to the substrate, the cyclic alkene vapor and transport gas is mixed with a flow of methyldiethoxysilane (M-DEOS) in a proportion of approximately 60% by weight M-DEOS and 40% by weight NBDE. This gas mixture is exposed to a plasma power of 250 W. The substrate is heated to 150° C. with a substrate bias of −15 VDC. A carbon doped silicon oxide film is deposited on the substrate using these conditions.

Example 6

The cyclic alkene, NBDE, stabilized with 100 ppm of 4-MCAT or 3-MOCAT is transferred, with the aid of helium pressure, from a stainless steel container through a chemical delivery line to a heated vaporizer at a flow rate of 1 mL/min. The cyclic alkene is vaporized into a chemical vapor process line that is heated to 80° C. and transported to a substrate using 500 sccm of helium as a transport gas with the system base pressure held at 6 torr. During transport to the substrate, the cyclic alkene vapor and transport gas is mixed with a flow of TMCTS in a proportion of approximately 60% TMCTS and 40% NBDE. This gas mixture is exposed to a plasma power of 250 W. The substrate is heated to 150° C. with a substrate bias of −15 VDC. A carbon doped silicon oxide film is deposited on the substrate using these conditions.

Example 7

This example employs the process in Example 5, however the carbon doped silicon oxide film is treated by a post-deposition curing step. The film is annealed at 425° C. under nitrogen for 4 hours to remove substantially all of the NBDE porogen that remains in the film. This treatment typically gives a slightly thinner film with a lower dielectric constant.

Example 8

This example employs the process in Example 6, however the carbon doped silicon oxide film is treated by a post-deposition curing step. The film is annealed at 425° C. under nitrogen for 4 hours to remove substantially all of the NBDE porogen that remains in the film. This treatment typically gives a slightly thinner film with a lower dielectric constant.

Example 9

This example employs the process in Example 5, however the cyclic alkene, NBDE, is stabilized with 50 ppm of 4-MCAT and 50 ppm of 3-MOCAT. A carbon doped silicon oxide film is deposited on the substrate.

Example 10

This example employs the process in Example 5, however the cyclic alkene, NBDE, is stabilized with 50 ppm of 4-MCAT and 50 ppm of BHT. A carbon doped silicon oxide film is deposited on the substrate.

Example 11

This example employs the process in Example 7, however the cyclic alkene, NBDE, is stabilized with 100 ppm of 3-isopropyl-1,2-dihydroxybenzene. A carbon doped silicon oxide film is deposited on the substrate.

Example 12

This example employs the process in Example 5, however the cyclic alkene, a 75:25 by weight mixture of NBDE and alpha-terpinene, is stabilized with 100 ppm of 3-isopropyl-1,2-dihydroxybenzene. A carbon doped silicon oxide film is deposited on the substrate.

Example 13

This example employs the process in Example 5, however the cyclic alkene, a 25:75 by weight mixture of dicyclopentadiene:alpha-terpinene, is stabilized with 100 ppm of 3-isopropyl-1,2-dihydroxybenzene. A carbon doped silicon oxide film is deposited on the substrate.

Example 14

This example employs the process in Example 8, however the cyclic alkene, NBDE, is stabilized with 200 ppm of 3-tert-butyl-4-methyl-1,2-dihydroxybenzene. A carbon doped silicon oxide film is deposited on the substrate.

Example 15

This example employs the process in Example 6, however the cyclic alkene, NBDE, is stabilized with 50 ppm of 4-MCAT. A carbon doped silicon oxide film is deposited on the substrate.

Example 16

This example employs the process in Example 7, however the cyclic alkene, NBDE, is stabilized with 150 ppm of 4-MCAT. A carbon doped silicon oxide film is deposited on the substrate.

Example 17

This example employs the process in Example 8, however the cyclic alkene, alpha-terpinene, is stabilized with 100 ppm of 4-MCAT. A carbon doped silicon oxide film is deposited on the substrate.

Example 18

This example employs the process in Example 5, however the cyclic alkene, limonene, is stabilized with 100 ppm of 4-MCAT. A carbon doped silicon oxide film is deposited on the substrate.

Example 19

This example employs the process in Example 5, however the cyclic alkene, alpha-pinene, is stabilized with 200 ppm of 4-MOCAT. A carbon doped silicon oxide film is deposited on the substrate.

Example 20

This example employs the process in Example 5, however the cyclic alkene, dicyclopentadiene, is stabilized with 150 ppm of 4-MCAT. A carbon doped silicon oxide film is deposited on the substrate.

Example 21

This example employs the process in Example 5, however the cyclic alkene, 1,4-dihydro-1,4-methanonaphthalene, is stabilized with 100 ppm of 3,4-dimethyl-1,2-dihydroxybenzene. A carbon doped silicon oxide film is deposited on the substrate.

Example 22

This example employs the process in Example 5, however the cyclic alkene vapor and transport gas is mixed with a flow of methyldiethoxysilane (M-DEOS) and a flow of tetramethyldisiloxane (TMDSO) in a proportion of approximately 40% by weight M-DEOS, 20% by weight TMDSO and 40% by weight NBDE. A carbon doped silicon oxide film is deposited on the substrate.

Example 23

This example employs the process in Example 5, however the cyclic alkene vapor and transport gas is mixed with a flow of methyldiethoxysilane (M-DEOS) and a flow of tetramethyldisiloxane (TMDSO) in a proportion of approximately 30% by weight M-DEOS, 30% by weight TMDSO and 40% by weight NBDE. A carbon doped silicon oxide film is deposited on the substrate.

Example 24

This example employs the process in Example 5, however the cyclic alkene vapor and transport gas is mixed with a flow of trimethylsilane (TMS) in a proportion of approximately 60% by weight TMS and 40% by weight NBDE. A carbon doped silicon oxide film is deposited on the substrate.

Example 25

This example employs the process in Example 5, however the cyclic alkene vapor and transport gas is mixed with a flow of fluorotriethoxysilane (FTES) in a proportion of approximately 60% by weight FTES and 40% by weight NBDE. A carbon doped silicon oxide film is deposited on the substrate.

Example 26

This example employs the process in Example 5, however the cyclic alkene vapor and transport gas is mixed with a flow of acryloxytrimethylsilane (AcroTMS) in a proportion of approximately 60% by weight AcroTMS and 40% by weight NBDE. A carbon doped silicon oxide film is deposited on the substrate.

Example 27

This example employs the process in Example 5, however the cyclic alkene vapor and transport gas is mixed with a flow of acetoxytrimethylsilane (AceTMS) in a proportion of approximately 60% by weight AceTMS and 40% by weight NBDE. A carbon doped silicon oxide film is deposited on the substrate.

Figure 4:
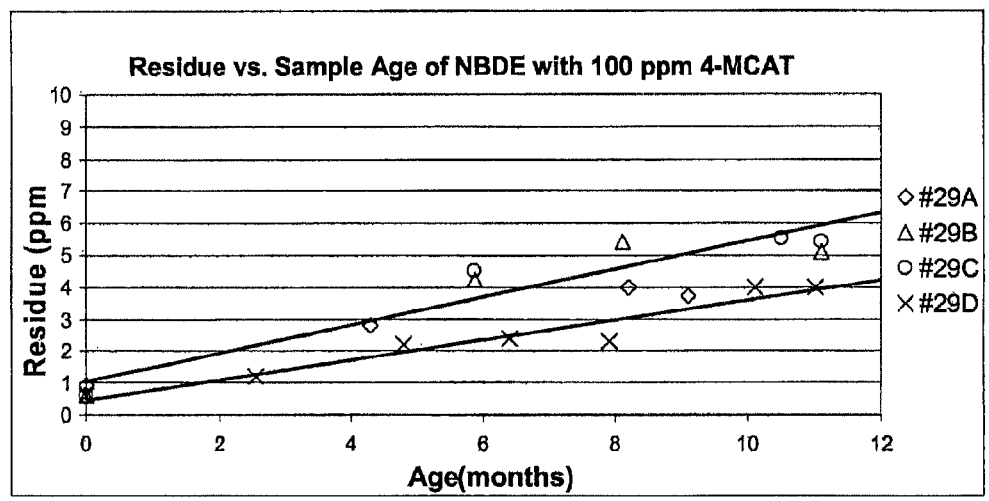
FIG. 4 is a plot showing the residue concentration of four samples of NBDE stabilized with 100 ppm of 4-MCAT as a function of sample age.
Figure 5:
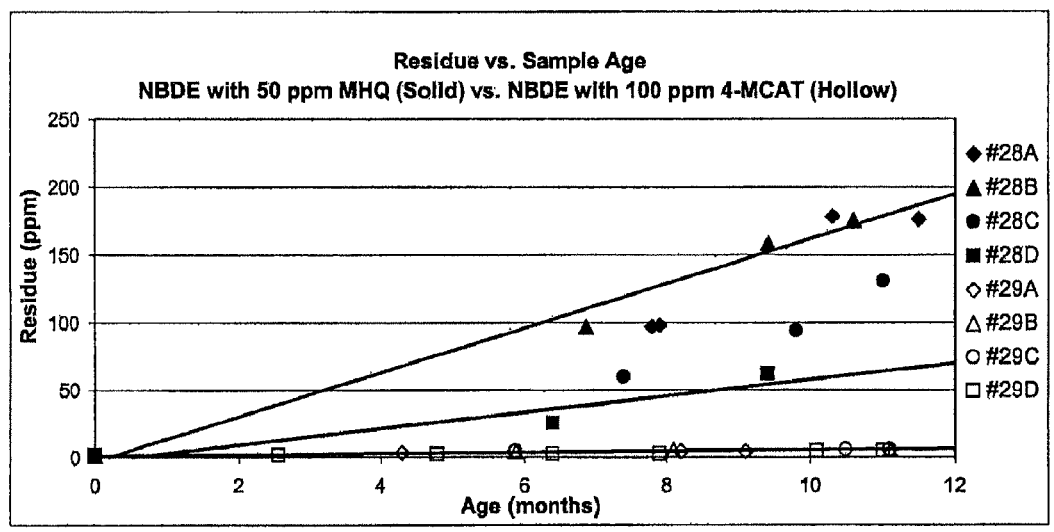
FIG. 5 is a plot including both plots shown in FIGS. 3 and 4.

A series of tests were devised to examine product shelf life under normal storage conditions over a one year timeframe. This is a key measure of long term stabilizer performance. Eight high purity stainless steel containers were filled in essentially the same manner from standard high volume production lots. Initial purity with respect to residue concentration was found to be nearly identical. The containers were sealed and were stored at approximately 25° C. ("room temperature") in an inert atmosphere under atmospheric pressure. Residue concentration was measured at the time of fill as a sample baseline, and then samples were pulled over the course of approximately one year in order to measure the increase in residue concentration. Residue concentration was measured as described in the above examples. The results are shown in FIGS. 3-5.

Example 28

Figure 3:
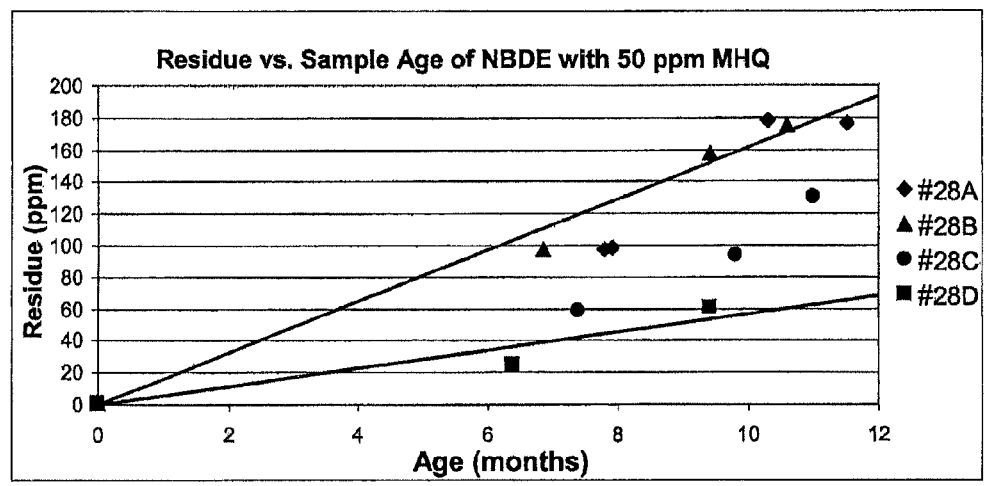
FIG. 3 is a plot showing the residue concentration of four samples of NBDE stabilized with 50 ppm of MHQ as a function of sample age.

FIG. 3 shows the residue concentration of four samples of NBDE stabilized with 50 ppm of MHQ as a function of sample age. Trend lines were used to highlight the highest and lowest concentration trends seen in the four samples. Based on these results, residue formation over time was approximately linear. Although the variation of the rate of residue formation between these samples was relatively large and not clearly understood, it was believed that small differences in oxygen concentration due to packaging and sampling may play a role. Using this data, one may reasonably predict that residue formed in a sample over the course of one year under similar storage conditions would vary from about 70 to about 190 ppm.

Example 29

FIG. 4 shows the residue concentration of four samples of NBDE stabilized with 100 ppm of 4-MCAT as a function of sample age. Trend lines again were used to highlight the highest and lowest concentration trends seen in the four samples. As seen with MHQ stabilized product, residue formation over time was approximately linear. However, residue concentration in the 4-MCAT stabilized samples under similar conditions was lower by at least an order of magnitude. In this case, the predicted residue after one year would vary from about 4 to about 6 ppm. Not only was the overall residue concentration lower, it was also more tightly distributed and therefore more predictable.

Example 30

The dramatic difference between the long term behavior of the MHQ and 4-MCAT stabilized products is most obvious when both studies are plotted on the same graph, as seen in FIG. 5. This figure clearly shows the differences both in range and in overall residue concentration formed over the same period.

General Purification Procedure #1

Cyclic alkene is purified by passing it through a filtration device that is charged with silica gel or alumina media in a manner to remove impurities such as water, alcohols, peroxides, stabilizers, stabilizer degradation products, oxygenated organic impurities and particulate matter.

General Purification Procedure #2

Cyclic alkene is charged into a distillation flask fitted with a distillation column, a condenser and two receiving vessels. One receiving vessel is designated for forerun, or more volatile fraction, and one receiving vessel is designated for collecting the main fraction, or high purity cyclic alkene. The distillation is operated under inert atmosphere at atmospheric pressure. A sufficient forerun fraction is collected to remove more volatile impurities, a main fraction is collected to separate out high purity cyclic alkene of desired purity, and the distillation process is terminated to leave behind a heel fraction of less volatile impurities.

General Purification Procedure #3

Cyclic alkene is charged into a distillation flask fitted with a distillation column, a condenser, two receiving vessels and a vacuum source. One receiving vessel is designated for forerun, or more volatile fraction, and one receiving vessel is designated for collecting the main fraction, or high purity cyclic alkene. The distillation is operated under inert atmosphere below atmospheric pressure to reduce the boiling point of the cyclic alkene to reduce or prevent thermal degradation during the distillation step. A sufficient forerun fraction is collected to remove more volatile impurities, a main fraction is collected to separate out high purity cyclic alkene of desired purity, and the distillation process is terminated to leave behind a heel fraction of less volatile impurities.

General Purification Procedure #4

Cyclic alkene is charged into a short path distillation system fitted with a heated zone, a condenser and two receiving vessels. One receiving vessel is designated for collecting the main fraction, or high purity cyclic alkene, and one receiving vessel is designated for receiving less volatile impurities. The distillation is operated under inert atmosphere at atmospheric pressure and is tuned to offer sufficient separation of high purity cyclic alkene from less volatile impurities.

General Purification Procedure #5

Cyclic alkene is charged into a short path distillation system fitted with a heated zone, a condenser and two receiving vessels. One receiving vessel is designated for collecting the main fraction, or high purity cyclic alkene, and one receiving vessel is designated for receiving less volatile impurities. The distillation is operated under inert atmosphere below atmospheric pressure to reduce the boiling point of the cyclic alkene to reduce or prevent thermal degradation during the distillation step. Further, the process is tuned to offer sufficient separation of high purity cyclic alkene from less volatile impurities.

General Stabilization Procedures

General Stabilization Procedure #1

An effective amount of stabilizer is charged into a product receiving vessel of a distillation system prior to distilling a high purity cyclic alkene into the receiving vessel. The distillation system is then operated to have the high purity cyclic alkene contact and solubilize the stabilizer as it is collected in the receiving vessel.

General Stabilization Procedure #2

An effective amount of a stabilizer is charged into a distillation system at a point between the condenser and product receiving vessel. The distillation system is then operated to have a high purity cyclic alkene contact and solubilize the stabilizer as it passes from the condenser to the receiving vessel.

General Stabilization Procedure #3

A distillation system is first operated to collect unstabilized high purity cyclic alkene in a receiving vessel without containing a stabilizer. An effective amount of the stabilizer is then charged into the receiving vessel in order to solubilize the stabilizer in the high purity cyclic alkene.

Example 31

The cyclic alkene, NBDE, is purified by employing General Purification Procedure #2 and stabilized with 100 ppm of 4-MCAT by employing General Stabilization Procedure #1.

Example 32

The cyclic alkene, NBDE, is purified by employing General Purification Procedure #3 and stabilized with 100 ppm of 4-MCAT by employing General Stabilization Procedure #1.

Example 33

The cyclic alkene, NBDE, is purified by employing General Purification Procedure #4 and stabilized with 100 ppm of 4-MCAT by employing General Stabilization Procedure #1.

Example 34

The cyclic alkene, NBDE, is purified by employing General Purification Procedure #5 and stabilized with 100 ppm of 4-MCAT by employing General Stabilization Procedure #1.

Example 35

The cyclic alkene, NBDE, is purified by employing General Purification Procedure #1 followed by General Purification Procedure #2 and stabilized with 100 ppm of 4-MCAT by employing General Stabilization Procedure #1.

Example 36

The cyclic alkene, NBDE, is purified by employing General Purification Procedure #1 followed by General Purification Procedure #3 and stabilized with 100 ppm of 4-MCAT by employing General Stabilization Procedure #1.

Example 37

The cyclic alkene, NBDE, is purified by employing General Purification Procedure #1 followed by General Purification Procedure #4 and stabilized with 100 ppm of 4-MCAT by employing General Stabilization Procedure #1.

Example 38

The cyclic alkene, NBDE, is purified by employing General Purification Procedure #1 followed by General Purification Procedure #5 and stabilized with 100 ppm of 4-MCAT by employing General Stabilization Procedure #1.

Example 38

The cyclic alkene, NBDE, is purified by employing General Purification Procedure #2 followed by General Purification Procedure #4 and stabilized with 100 ppm of 4-MCAT by employing General Stabilization Procedure #1.

Example 38

The cyclic alkene, NBDE, is purified by employing General Purification Procedure #3 followed by General Purification Procedure #5 and stabilized with 100 ppm of 4-MCAT by employing General Stabilization Procedure #1.

Example 39

The cyclic alkene, NBDE, is purified by employing General Purification Procedure #1 followed by General Purification Procedure #2 followed by General Purification Procedure #4 and stabilized with 100 ppm of 4-MCAT by employing General Stabilization Procedure #1.

Example 40

The cyclic alkene, NBDE, is purified by employing General Purification Procedure #2 and stabilized with 100 ppm of 4-MCAT by employing General Stabilization Procedure #2.

Example 41

The cyclic alkene, NBDE, is purified by employing General Purification Procedure #2 and stabilized with 100 ppm of 4-MCAT by employing General Stabilization Procedure #3.

While we have shown and described several embodiments in accordance with the present disclosure, it is to be clearly understood that the same are susceptible to numerous changes apparent to one skilled in the art. Therefore, we do not wish to be limited to the details shown and described but intend to show all changes and modifications which come within the scope of the appended claims.

All publications, patent applications, patents, and other references mentioned herein are incorporated by reference in their entirety.

What is claimed is:

1. A process, comprising treating a substrate in a film deposition chamber with at least one cyclic alkene composition and at least one silicon containing compound in a chemical vapor deposition process to form a carbon doped silicon oxide film on the substrate,
wherein the cyclic alkene composition comprises:
(a) one or more substituted or unsubstituted cyclic alkenes, and
(b) an antioxidant composition comprising at least one compound of Formula (I),

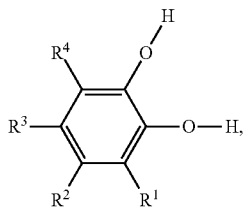

wherein $R^1$ through $R^4$ each independently is H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl, and with the proviso that at least one of $R^1$ through $R^4$ is not H, and that, if one of $R^1$ through $R^4$ is t-butyl, at least one of the remaining $R^1$ through $R^4$ is not H.

2. The process of claim 1, further comprising, prior to the treatment step, providing the cyclic alkene composition in a first container, the silicon containing compound in a second container, a film deposition tool containing the film deposition chamber, a connector configured to connect the first and second containers to the film deposition chamber within the film deposition tool, and a stream of carrier gas to sweep the cyclic alkene composition and the silicon containing compound through the connector into the film deposition chamber.

3. The process of claim 2, further comprising, prior to the treatment step, introducing vapors of the cyclic alkene composition and the silicon containing compound into the carrier gas stream.

4. The process of claim 3, further comprising, prior to the treatment step, transporting the vapors of the cyclic alkene composition and silicon containing compound into the film deposition chamber via the carrier gas stream.

5. The process of claim 1, wherein one of $R^1$ through $R^4$ is methyl, ethyl, methoxy, or ethoxy.

6. The process of claim 5, wherein at least one of the remaining $R^1$ through $R^4$ is H.

7. The process of claim 6, wherein all of the remaining $R^1$ through $R^4$ are H.

8. The process of claim 1, wherein $R^2$ or $R^3$ is methyl or methoxy.

9. The process of claim 8, wherein at least one of the remaining $R^1$ through $R^4$ is H.

10. The process of claim 1, wherein the antioxidant composition comprises 4-methyl-1,2-dihydroxybenzene.

11. The process of claim 1, wherein the antioxidant composition comprises 3-methoxy-1,2-dihydroxybenzene.

12. The process of claim 1, wherein the antioxidant composition is present in a concentration between about 1 ppm and about 200 ppm.

13. The process of claim 1, wherein the antioxidant composition is present in a concentration between about 50 ppm and about 150 ppm.

14. The process of claim 1, wherein the cyclic alkene has the general formula $C_1H_{2n-2x-y}R_y$, in which n is the number of carbons in the primary cyclic structure and is an integer from 4 to 18, x is the number of unsaturated sites in the primary cyclic structure and is an integer and $1 \leq x \leq n/2$, y is the number of substituents, R, on the primary cyclic structure and is an integer and $0 \leq y \leq 2n-2x$, and each R independently is $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent.

15. The process of claim 1, wherein the cyclic alkene has the general formula $C_nH_{2-(2x+2)-y}R_y$, in which n is the number of carbons in the primary cyclic structure and is an integer from 5 to 18, x is the number of unsaturated sites in the primary cyclic structure and is an integer and $x \leq n/2$, y is the number of substituents, R, on the primary cyclic structure and is an integer and $0 \leq y \leq 2n-(2x+2)$, and each R independently is $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent.

16. The process of claim 1, wherein the cyclic alkene has the general formula $C_nH_{2n-(2x+4)-y}R_y$, in which n is the number of carbons in the primary cyclic structure and is an integer from 7 to 18, x is the number of unsaturated sites in the primary cyclic structure and is an integer and $x \leq n/2$, y is the number of substituents, R, on the primary cyclic structure and is an integer and $0 \leq y \leq 2n-(2x+4)$, each R independently is $C_1$-$C_{18}$ linear alkyl, $C_3$-$C_{18}$ branched alkyl, $C_2$-$C_{18}$ unsaturated alkyl, $C_3$-$C_{18}$ cyclic alkyl, $C_1$-$C_{18}$ linear alkoxy, $C_3$-$C_{18}$ branched alkoxy, $C_2$-$C_{18}$ unsaturated alkoxy, $C_3$-$C_{18}$ cyclic alkoxy, substituted or unsubstituted aryl, or substituted silicon containing substituent.

17. The process of claim 1, wherein the cyclic alkene is at least one compound selected from the group consisting of dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene.

18. The process of claim 1, wherein at least one of $R^1$ through $R^4$ is not H, or if one of $R^1$ through $R^4$ is t-butyl, at least one of the remaining $R^1$ through $R^4$ is not H.

19. A process, comprising treating a substrate in a film deposition chamber with at least one cyclic alkene composition and at least one silicon containing compound in a chemical vapor deposition process to form a carbon doped silicon oxide film on the substrate,
wherein the cyclic alkene composition comprises:
(a) a cyclic alkene selected from the group consisting of dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene, and
(b) an antioxidant composition comprising 4-methyl-1,2-dihydroxybenzene or 3-methoxy-1,2-dihydroxybenzene.

20. A process, comprising:
storing a cyclic alkene composition in a sealed container for at least 6 months, and
after storing the cyclic alkene composition, using the cyclic alkene composition together with at least one silicon-containing compound in a chemical vapor deposition process to form a carbon doped silicon oxide film on a substrate,
wherein the cyclic alkene composition comprises:
(a) at least one substituted or unsubstituted cyclic alkene, and
(b) an antioxidant composition comprising at least one compound of Formula (I),

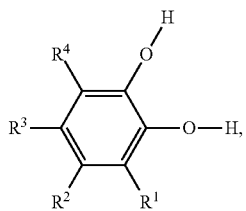

(I)

wherein $R^1$ through $R^4$ each independently is H, $C_1$-$C_8$ linear alkyl, $C_2$-$C_8$ unsaturated alkyl, $C_3$-$C_8$ branched alkyl, $C_3$-$C_8$ cyclic alkyl, $C_1$-$C_8$ linear alkoxy, $C_2$-$C_8$ unsaturated alkoxy, $C_3$-$C_8$ branched alkoxy, $C_3$-$C_8$ cyclic alkoxy or substituted or unsubstituted aryl.

* * * * *

UNITED STATES PATENT AND TRADEMARK OFFICE
CERTIFICATE OF CORRECTION

| | | |
|---|---|---|
| PATENT NO. | : 8,252,704 B2 | |
| APPLICATION NO. | : 13/179977 | |
| DATED | : August 28, 2012 | |
| INVENTOR(S) | : Daniel J. Teff and John L. Chagolla | |

It is certified that error appears in the above-identified patent and that said Letters Patent is hereby corrected as shown below:

Column 33, Line 18
In Claim 1, delete "one or more" and insert -- at least one -- therefor.

Column 33, Line 18
In Claim 1, delete "alkenes," and insert -- alkene, -- therefor.

Column 34, Line 14 (Approx.)
In Claim 14, delete "$C_1H_{2n-2x-y}R_y$," and insert -- $C_nH_{2n-2x-y}R_y$, -- therefor.

Column 34, Line 27
In Claim 15, delete "$C_nH_{2-(2x+2)-y}R_y$," and insert -- $C_nH_{2n-(2x+2)-y}R_y$, -- therefor.

Signed and Sealed this
Twenty-third Day of October, 2012

David J. Kappos
*Director of the United States Patent and Trademark Office*